US006664091B2

(12) United States Patent
Curtis et al.

(10) Patent No.: US 6,664,091 B2
(45) Date of Patent: Dec. 16, 2003

(54) 53010, A HUMAN CARBOXYLESTERASE FAMILY MEMBER AND USES THEREOF

(75) Inventors: Rory A. J. Curtis, Southborough, MA (US); Inmaculada Silos-Santiago, Jamaica Plain, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 10/023,515

(22) Filed: Dec. 18, 2001

(65) Prior Publication Data

US 2002/0182636 A1 Dec. 5, 2002

Related U.S. Application Data

(60) Provisional application No. 60/256,369, filed on Dec. 18, 2000, and provisional application No. 60/279,508, filed on Mar. 28, 2001.

(51) Int. Cl.$^7$ .............................. C12N 9/18; C12N 1/20; C12N 15/00

(52) U.S. Cl. ............... 435/197; 435/252.3; 435/252.33; 435/320.1; 435/325; 536/23.2

(58) Field of Search ........................... 435/197, 252.33, 435/252.3, 320.1, 325; 536/23.2

(56) References Cited

U.S. PATENT DOCUMENTS 6,063,610 A * 5/2000 Silver ......................... 435/197

FOREIGN PATENT DOCUMENTS

| WO | WO 01/64835 A2 | 9/2001 |
| WO | WO 02/06454 A | 1/2002 |
| WO | WO 02/46426 A | 6/2002 |
| WO | WO 02/50105 A | 6/2002 |

OTHER PUBLICATIONS

Tsukamoto T, Toyama R, et al Structure of the human gene and two rat cDNAs encoding the alpha chain of GTP–binding regulatory protein Go: two different mRNAs are generated by alternative splicing. Proc Natl Acad Sci U S A. Apr. 1991 15;88(8):2974–8.*
Silver et al, No. 6063610e1 Carboxylesterase nucleic acide: molecules, proteins and uses thereof. US 6,063,610 SEQ ID No.: 10. May 16, 2000 (FD Dec. 12, 1996). Alignment with SEQ ID No.: 2.*
Hillier et al. WashU–NIC human EST Project. Similar to Carboxylesterase precursor. EMBL ACC# AA608798. Mar. 2, 1998. Alignment with SEQ ID No.: 2.*
Old and Primrose. Nucelic acid hybridization methods. In: Principiles of Gene Manipulation. Blackwell Sci Pubs, Boston, 1985. pp. 117–120.*
Tsukamoto, T., Toyama, R. et al, Human guanine nucleotide–binding regulatory protein (Go–alpha) gene, exons 1 and 2. Nov. 8, 1994 GeneBank Acc# M60156.*
Bruce, D., Mundt, M. et al, Homo sapiens chromosome 16 clone 449J19. May 6, 1999 GeneBank Acc# AC007499.*
Altschul et al., "Basic Local Alignment Search Tool," J. Mol. Biol. 215:403–410 (1990).
Altschul et al., "Gapped BLAST and PSI_BLAST: a new generation of protein database search programs," Nucleic Acids Research, 25(17):3389–3402 (1997).
Begley et al., "A Conserved Motif within the Vitamin K–dependent Carboxylase Gene is Widely Distributed across Animal Phyla," Journal of Biological Chemistry 275(46):36245–36249 (Nov. 17, 2000).
Chanda (ed.), Current Protocols in Molecular Biology, 2000, vol. 4, John Wiley & Sons, Inc. (Table of Contents only).
Grifman et al., "Functional redundancy of acetylcholinesterase and neuroligin in mammalian neuritogenesis," Proc. Natl. Acad. Sci. USA 95:13935–13940 (Nov. 1998).
International Human Genome Sequencing Consortium, "Initial sequencing and analysis of the human genome," Nature 409:860–921 (Feb. 15, 2001).
Karlin et al., "Applications and statistics for multiple high–scoring segments in molecular sequences," Proc. Natl. Acad. Sci., 90:5873–5877 (Jun. 1993).
Karlin et al., "Methods for assessing the statistical significance of molecular sequence features by using general scoring schemes," Proc. Natl. Acad. Sci., 87:2264–2268 (Mar. 1990).
Myers et al., "Optimal alignments in linear space," CABIOS, 4(1):11–17 (1998).
Sambrook et al. (eds.), "Molecular Cloning—A Laboratory Manual," 1989, $2^{nd}$ Edition, Cold Spring Harbor Laboratory Press (Table of Contents only).
Sonnhamer et al., "Pfam: A Comprehensive Database of Protein Domain Families Based on Seed Alignments," Proteins 28:405–420 (1997).
Venter et al., "The Sequence of the Human Genome," Science 291:1304–1351 (Feb. 16, 2001).
Walker et al., "On a Potential Global Role for Vitamin K–dependent γCarboxylation in Animal Systems," Journal of Biological Chemistry 276(11):7769–7774 (Mar. 16, 2001).

(List continued on next page.)

*Primary Examiner*—Rebecca E. Prouty
*Assistant Examiner*—Sheridan L. Swope
(74) *Attorney, Agent, or Firm*—Millennium Pharmaceuticals, Inc.

(57) ABSTRACT

The invention provides isolated nucleic acids molecules, designated 53010 nucleic acid molecules, which encode novel carboxylesterase members. The invention also provides antisense nucleic acid molecules, recombinant expression vectors containing 53010 nucleic acid molecules, host cells into which the expression vectors have been introduced, and nonhuman transgenic animals in which a 53010 gene has been introduced or disrupted. The invention still further provides isolated 53010 proteins, fusion proteins, antigenic peptides and anti-53010 antibodies. Diagnostic methods utilizing compositions of the invention are also provided.

5 Claims, 3 Drawing Sheets

OTHER PUBLICATIONS

Weintraub et al., "Anti-sense RNA as a molecular tool for genetic analysis," Trends in Genetics, 1(1):22–25 (Jan. 1985).

GenBank™ Accession No. L05493 (Aug. 4, 1993).

GenBank™ Accession No. Q04791 (May 30, 2000).

Bruce et al. (1999), Homo sapiens chromosome 16 clone RP11–165M2, EBI Database Acession No. AC 007335 XP 002222742.

Hashimoto et al. (2001), Macaca fasciculris brain cDNA clone: QtrA–12316, EBI Database Acession No. AB 060873 XP 00222744.

Isogai et al. (2001), Homo sapiens cDNA FLJ31547 fis, clone NT2RI2001010, EBI Database Acession No. AK 056109 XP 002222743.

National Institutes of Health (2001), 603039938F1 NIH_MGC_115 Homo sapiens cDNA clone IMAGE: 5181056 5' mRNA sequence, EBI Database Acession No. BI 822069 XP002222745.

Sone et al. (1998), Carboxylesterase precursor (EC 3.1.1.1), EBI Database Acession No. 035533 XP 02222746.

Satoh et al., "Molecular Aspects of Carboxylesterase Isoforms in Comparison with Other Exterases," Toxicology Letters, 82/83: 439–445 (1995).

PCT Foreign Search Report (Nov. 12, 2002).

* cited by examiner-

COesterase: domain 1 of 1, from 44 to 545: score 552.8, E = 2.3e-162
(SEQ ID NO:4)     *->GkvrGvnektdngeqsvysFlGIPYAePPVGnLRFkaPqPYkepWsd
                     G + G+++++ +     +v++FlG+P+A PP+G+LRF +PqP + pW++
Fbh53010FL   44   GWIQGKQVTVLGSPVPVNVFLGVPFAAPPLGSLRFTNPQP-ASPWDN   89 vldAtkyppsClQdddfgfslsdLKvalkmlslgwnklvglklsEDCLYL
                  + At+yp+ ClQ++++   +     +   + +   g    sEDCLYL
Fbh53010FL   90   LREATSYPNLCLQNSEWLLLDQH------MLKVHYPKFG--VSEDCLYL  130

NVytPkntkpnsklPVmVwIhGGGFmfGsghslplslYdgeslaregnVI
                  N+y P+ +   +sklPV+Vw +GG+F +Gs+        s   dg++la+ ++V
Fbh53010FL  131   NIYAPAHADTGSKLPVLVWFPGGAFKTGSA-----SIFDGSALAAYEDVL  175 vVsiNYRLGplGFLstgddklpgsGNyGLlDQrlALkWVqdNIaaFGGDP
                  vV ++YRLG++GF+++t d ++p   GN++++DQ++AL WVq+NI  FGGDP
Fbh53010FL  176   VVVVQYRLGIFGFFTTWDQHAP--GNWAFKDQVAALSWVQKNIEFFGGDP  223 nsVTifGeSAGaaSVsllllsngGDNppsskgLFhRAIsqSGsalspwai
                  +sVTifGeSAGa   SVs l+ls      p++kgLFh+AI++SG a+ p
Fbh53010FL  224   SSVTIFGESAGAISVSSLILS------PMAKGLFHKAIMESGVAIIPYLE  267 qsesnargrakelarllGCnetsssselldCLRsksaeeLleatrsfllfe
                  ++     + +a + G n ++s++ll+CLR k+++eLl     ++++
Fbh53010FL  268   AHDYEKSEDLQVVAHFCGNNASDSEALLRCLRTKPSKELLTLSQ--KTKS  315

Fig. 2A

```
Fbh53010FL  316  ---FTR------VVDGA-----FFPNEPLDLLSQKAFKAIPSIIGVNNH  350
                    f+       vvDG+          f+p +P++l+ ++ f+ +P +iGv+++
                 yvpflplflaFgPvvDGdDapeafipedPeelikeGkfadvPyliGvtkd Fbh53010FL  351  ECGFLLPMkEAPEILSG-----------SNKSLALHLIQNILHIPPQ--  386
                    E+g++++m+++++++ +g             ++ l++ l+ ++ +
                 EGgyfaam.llnasskgedelkketnpdvwlelikyllfyasealnikdM Fbh53010FL  387  --YLHLVANEYFHD-KH-SLTEIRDSLLDLLGDVFFVVP-ALITARYHRD  431
                    ++  v  ++Y+ d -  s + +++  l+d+l+D++F++p ++  ++ +++
                 ddladkvlekYpgdvddfsvesrkpnlqdmltDllFkcptrvaadlhakh Fbh53010FL  432  AGAPVYFYEFRHRPQC------FEDTKPAFVKADHADEVRFVFGGAFLKG  475
                    +g+PvY+Y+f+h+++       +++p f++a+H+dE++fvFg   +lk+
                 ggsPvYaYvfdhpasfgigQflakrvdpefggavHgdEiffvFgnpllke Fbh53010FL  476  DIVMFegATEEEKLLSRKMKYWATFARTGNP-NGN--DLSLWPAYNLTE  522
                    +   ++++eeek++s++mm++ywa+FA+tGnP ng   l  Wp+y+ +e
                 qlyka..teeeekssssktmmnywanFAktGnPnngtsnglvvWpkytsee Fbh53010FL  523  Q--YLQLDLNMSLGQRLKEPR-----VDFW  545
                    q   +l+ l +  q+lk+ +      ++fw
                 qkYsllilltttitaqklkardprkvlcnfw<-*
```

53010, A HUMAN CARBOXYLESTERASE FAMILY MEMBER AND USES THEREOF

RELATED APPLICATIONS

This application claims priority to U.S. provisional application No. 60/256,369, filed on Dec. 18, 2000, and U.S. provisional application No. 60/279,508, filed on Mar. 28, 2001, the contents of which are incorporated herein by reference.

BACKGROUND OF THE INVENTION

Higher eukaryotes have many distinct esterases. Among the different types of esterases are those that act on carboxylic esters, also known as carboxylesterases. Carboxylesterases have been classified into three categories (A, B and C) on the basis of differential patters of inhibition by organophosphates (Myers et al. (1988) Mol. Biol. Evol. 5(2):113–119). Sequence analysis of a number of type-B carboxylesterase demonstrates their evolutionary interrelatedness. Members of the type B carboxylesterase family include acetylcholincarboxylesterases, mammalian cholincarboxylesterases, thyroglobulin, neuroligins, and mammalian bile salt activated lipases.

The type B family of carboxylesterase also includes vitamin K-dependent carboxylases. Vitamin K-dependent gamma-glutamyl carboxylases catalyze the posttranslational conversion of glutamic acid to gamma-carboxyglutamic acid, an amino acid critical to the function of the vitamin K-dependent blood coagulation proteins (Begley et al. (2000) J. Biol. Chem. 275:36245–36249). Incomplete gamma carboxylation of blood clotting factors is associated with poor coagulation.

For the gamma carboxylation event to occur, both vitamin K and the presence of a gamma carboxylation recognition site on the substrate are required. Gamma carboxyglutamic acid confers calcium binding ability upon the modified protein. For blood clotting factors, calcium binding results in a conformational change that exposes hydrophobic residues for interactions with membranes.

Although gamma carboxylation was a biochemical event first characterized in the mammalian blood clotting cascade, it has been found to have a more generalized applicability. For example, vitamin K-dependent gamma carboxylation of glutamate residues has also been detected for a variety of other proteins including bone proteins, PRGP1, PRGP2, and neuropeptides (Walker et al. (2000) J. Biol. Chem., December 7 epub ahead of print).

SUMMARY OF THE INVENTION

The present invention is based, in part, on the discovery of a novel carboxylesterase family member, referred to herein as "53010." The nucleotide sequence of a cDNA encoding 53010 is shown in SEQ ID NO:1, and the amino acid sequence of a 53010 polypeptide is shown in SEQ ID NO:2. In addition, the nucleotide sequences of the coding region are depicted in SEQ ID NO:3.

Accordingly, in one aspect, the invention features a nucleic acid molecule that encodes a 53010 protein or polypeptide, e.g., a biologically active portion of the 53010 protein. In a preferred embodiment the isolated nucleic acid molecule encodes a polypeptide having the amino acid sequence of SEQ ID NO:2. In other embodiments, the invention provides isolated 53010 nucleic acid molecules having the nucleotide sequence shown in SEQ ID NO:1, SEQ ID NO:3, a full complement of SEQ ID NO:1 or SEQ ID NO:3. In still other embodiments, the invention provides nucleic acid molecules that are substantially identical (e.g., naturally occurring allelic variants) to the nucleotide sequence shown in SEQ ID NO:1, SEQ ID NO:3. In other embodiments, the invention provides a nucleic acid molecule which hybridizes under a stringency condition described herein to a nucleic acid molecule comprising the nucleotide sequence of SEQ ID NO:1, SEQ ID NO:3, wherein the nucleic acid encodes a full length 53010 protein or an active fragment thereof.

In a related aspect, the invention further provides nucleic acid constructs that include a 53010 nucleic acid molecule described herein. In certain embodiments, the nucleic acid molecules of the invention are operatively linked to native or heterologous regulatory sequences. Also included, are vectors and host cells containing the 53010 nucleic acid molecules of the invention e.g., vectors and host cells suitable for producing 53010 nucleic acid molecules and polypeptides.

In another related aspect, the invention provides nucleic acid fragments suitable as primers or hybridization probes for the detection of 53010-encoding nucleic acids.

In still another related aspect, isolated nucleic acid molecules that are antisense to a 53010 encoding nucleic acid molecule are provided.

In another aspect, the invention features, 53010 polypeptides, and biologically active or antigenic fragments thereof that are useful, e.g., as reagents or targets in assays applicable to treatment and diagnosis of 53010-mediated or -related disorders. In another embodiment, the invention provides 53010 polypeptides having a 53010 activity. Preferred polypeptides are 53010 proteins including at least one carboxylesterase domain, and, preferably, having a 53010 activity, e.g., a 53010 activity as described herein.

In other embodiments, the invention provides 53010 polypeptides, e.g., a 53010 polypeptide having the amino acid sequence shown in SEQ ID NO:2 or; an amino acid sequence that is substantially identical to the amino acid sequence shown in SEQ ID NO:2; or an amino acid sequence encoded by a nucleic acid molecule having a nucleotide sequence which hybridizes under a stringency condition described herein to a nucleic acid molecule comprising the nucleotide sequence of SEQ ID NO:1, SEQ ID NO:3, wherein the nucleic acid encodes a full length 53010 protein or an active fragment thereof.

In a related aspect, the invention further provides nucleic acid constructs which include a 53010 nucleic acid molecule described herein.

In a related aspect, the invention provides 53010 polypeptides or fragments operatively linked to non-53010 polypeptides to form fusion proteins.

In another aspect, the invention features antibodies and antigen-binding fragments thereof, that react with, or more preferably specifically bind 53010 polypeptides or fragments thereof, e.g., a carboxylesterase domain.

In another aspect, the invention provides methods of screening for agents, e.g., compounds, that modulate the expression or activity of the 53010 polypeptides or nucleic acids, e.g., compounds that modulate the normal pain response, aberrant or altered pain response, or neurological response.

In a preferred embodiment, the effect of an agent, e.g., a compound, on the pain response is evaluated by an analgesic test, e.g., the hot plate test, tail flick test, writhing test, paw pressure test, all electric stimulation test, tail withdrawal test, or formalin test.

In a preferred embodiment, the agent, e.g., compound, inhibits 53010 activity.

In still another aspect, the invention provides a process for modulating 53010 polypeptide or nucleic acid expression or activity, e.g. using the screened compounds. In certain embodiments, the methods involve treatment of conditions related to aberrant, e.g., decreased or increased expression of the 53010 polypeptides or nucleic acids, such as conditions involving pain response, aberrant or altered pain response, or pain related disorders.

In still another aspect, the invention features a method of modulating (e.g., enhancing or inhibiting) an activity of a cell (e.g., a neural cell), or a response (e.g., a pain response) in a subject. The method includes contacting the cell with, or administered to the subject, an agent, e.g., a compound, that modulates the activity or expression of a 53010 polypeptide or nucleic acid, in an amount effective to modulate the activity or the response.

In a preferred embodiment, the agent modulates (e.g., increases or decreases) carboxylesterase activity.

In a preferred embodiment, the agent modulates (e.g., increases or decreases) expression of the 53010 nucleic acid by, e.g., modulating transcription, mRNA stability, etc.

In a preferred embodiment, the cell, e.g., the 53010-expressing cell, is a central or peripheral nervous system cell, e.g., a cell in an area involved in pain control, e.g., a cell in the brain or spinal cord.

In a preferred embodiment, the agent, e.g., the compound, and the 53010-polypeptide or nucleic acid are contacted in vitro or ex vivo. In a preferred embodiment, the contacting step is effected in vivo in a subject, e.g., as part of a therapeutic or prophylactic protocol. The contacting or administering step(s) can be repeated.

Preferably, the subject is a human, e.g., a patient with pain or a pain-associated disorder disclosed herein. For example, the subject can be a patient with pain elicited from tissue injury, e.g., inflammation, infection, ischemia; pain associated with musculoskeletal disorders, e.g., joint pain; tooth pain; headaches, e.g., migrane; pain associated with surgery; pain related to inflammation, e.g., irritable bowel syndrome; or chest pain. The subject can be a patient with complex regional pain syndrome (CRPS), reflex sympathetic dystrophy (RSD), causalgia, neuralgia, central pain and dysesthesia syndrome, carotidynia, neurogenic pain, refractory cervicobrachial pain syndrome, myofascial pain syndrome, craniomandibular pain dysfunction syndrome, chronic idiopathic pain syndrome, Costen's pain-dysfunction, acute chest pain syndrome, gynecologic pain syndrome, patellofemoral pain syndrome, anterior knee pain syndrome, recurrent abdominal pain in children, colic, low back pain syndrome, neuropathic pain, phantom pain from amputation, phantom tooth pain, or pain asymbolia. The subject can be a cancer patient, e.g., a patient with brain cancer, bone cancer, or prostate cancer. In other embodiments, the subject is a non-human animal, e.g., an experimental animal, e.g., an arthritic rat model of chronic pain, a chronic constriction injury (CCI) rat model of neuropathic pain, or a rat model of unilateral inflammatory pain by intraplantar injection of Freund's complete adjuvant (FCA).

In other embodiments, the subject is a human, e.g., a patient with infertility. The subject can be a cancer patient, e.g., a patient with prostate cancer. In yet other embodiments, the subject is a non-human animal, e.g., an experimental animal, e.g., a rodent model for infertility.

In preferred embodiments, the agent is a peptide, a phosphopeptide, a small molecule, e.g., a member of a combinatorial library, or an antibody, or any combination thereof. The antibody can be conjugated to a therapeutic moiety selected from the group consisting of a cytotoxin, a cytotoxic agent and a radioactive metal ion.

In additional preferred embodiments, the agent is an antisense molecule, a ribozyme, a triple helix molecule, or a 53010 nucleic acid, or any combination thereof.

In a preferred embodiment, the agent is administered in combination with a cytotoxic agent.

In another aspect, the invention features a method of treating or preventing, in a subject, a 53010-associated disorder. The method includes administering to the subject, e.g., a subject at risk of, or afflicted with, a 53010-associated disorder, an agent, e.g., a compound as described herein, that modulates the activity or expression of a 53010 polypeptide or nucleic acid, in an amount effective to treat or prevent the disorder.

In a preferred embodiment, the disorder is pain or a pain related disorder.

In a preferred embodiment, the subject is a subject as described herein, e.g., a human.

In still another aspect, the invention features a method for evaluating the efficacy of a treatment of a disorder, e.g., a disorder disclosed herein, in a subject. The method includes treating a subject with a protocol under evaluation; assessing the expression of a 53010 nucleic acid or 53010 polypeptide, such that a change in the level of 53010 nucleic acid or 53010 polypeptide after treatment, relative to the level before treatment, is indicative of the efficacy of the treatment of the disorder.

In a preferred embodiment, the disorder is pain or a pain related disorder.

In a preferred embodiment, the subject is a human.

The invention also features a method of diagnosing a disorder, e.g., a disorder disclosed herein, in a subject. The method includes evaluating the expression or activity of a 53010 nucleic acid or a 53010 polypeptide, such that, a difference in the level of 53010 nucleic acid or 53010 polypeptide relative to a normal subject or a cohort of normal subjects is indicative of the disorder.

In a preferred embodiment, the disorder is pain or a pain related disorder.

In a preferred embodiment, the subject is a human.

In a preferred embodiment, the evaluating step occurs in vitro or ex vivo. For example, a sample, e.g., a blood sample, is obtained from the subject.

In a preferred embodiment, the evaluating step occurs in vivo. For example, by administering to the subject a detectably labeled agent that interacts with the 53010 nucleic acid or polypeptide, such that a signal is generated relative to the level of activity or expression of the 53010 nucleic acid or polypeptide.

The invention also provides assays for determining the activity of or the presence or absence of 53010 polypeptides or nucleic acid molecules in a biological sample, including for disease diagnosis.

In further aspect, the invention provides assays for determining the presence or absence of a genetic alteration in a 53010 polypeptide or nucleic acid molecule, including for disease diagnosis.

In yet another aspect, the invention features a method for identifying an agent, e.g., a compound, which modulates the activity of a 53010 polypeptide, e.g., a 53010 polypeptide as described herein, or the expression of a 53010 nucleic acid, e.g., a 53010 nucleic acid as described herein, including contacting the 53010 polypeptide or nucleic acid with a test agent (e.g., a test compound); and determining the effect of the test compound on the activity of the 53010 polypeptide or nucleic acid to thereby identify a compound which modulates the activity of the 53010 polypeptide or nucleic acid.

In a preferred embodiment, the activity of the 53010 polypeptide is a carboxylesterase activity.

In a preferred embodiment, the activity of the 53010 polypeptide is modulation of pain response.

In preferred embodiments, the agent is a peptide, a phosphopeptide, a small molecule, e.g., a member of a combinatorial library, or an antibody, or any combination thereof.

In additional preferred embodiments, the agent is an antisense, a ribozyme, or a triple helix molecule, or a 53010 nucleic acid, or any combination thereof.

In another aspect, the invention features a two dimensional array having a plurality of addresses, each address of the plurality being positionally distinguishable from each other address of the plurality, and each address of the plurality having a unique capture probe, e.g., a nucleic acid or peptide sequence. At least one address of the plurality has a capture probe that recognizes a 53010 molecule. In one embodiment, the capture probe is a nucleic acid, e.g., a probe complementary to a 53010 nucleic acid sequence. In another embodiment, the capture probe is a polypeptide, e.g., an antibody specific for 53010 polypeptides. Also featured is a method of analyzing a sample by contacting the sample to the aforementioned array and detecting binding of the sample to the array.

Other features and advantages of the invention will be apparent from the following detailed description, and from the claims.

BRIEF DESCRIPTION OF THE DRAWINGS

FIGS. 2A–2B depict an alignment of the carboxylesterase domain of human 53010 with a consensus amino acid sequence derived from a hidden Markov model (HMM) from PFAM. The upper sequence is the consensus amino acid sequence (SEQ ID NO:4), while the lower amino acid sequence corresponds to amino acids 44 to 545 of SEQ ID NO:2.

DETAILED DESCRIPTION

Figure 1:
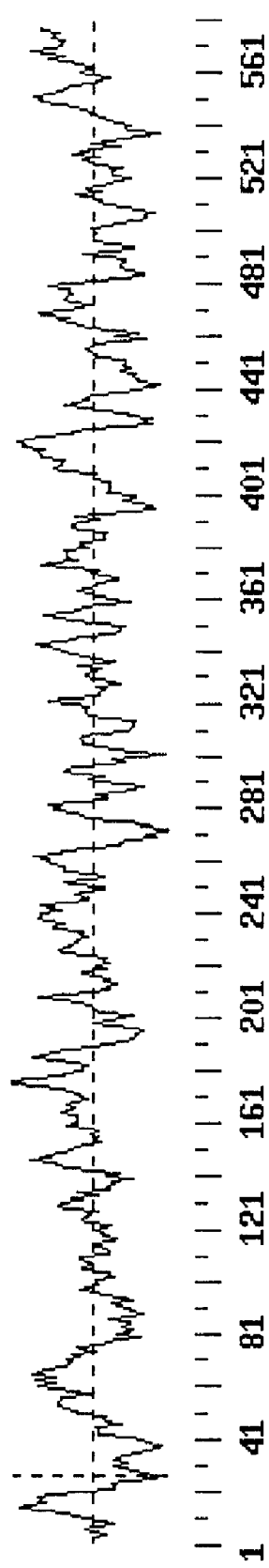
FIG. 1 depicts a hydropathy plot of human 53010. Relative hydrophobic residues are shown above the dashed horizontal line, and relative hydrophilic residues are below the dashed horizontal line. Numbers corresponding to positions in the amino acid sequence of human 53010 are indicated. Polypeptides of the invention include fragments which include: all or part of a hydrophobic sequence, i.e., a sequence above the dashed line, e.g., the sequence from about amino acid 51 to 80, from about 140 to 152, from about 232 to 248, and from about 410 to 435 of SEQ ID NO:2; all or part of a hydrophilic sequence, i.e., a sequence below the dashed line, e.g., the sequence of from about amino acid 190 to 205, from about 265 to 281, and from about 440 to 458 of SEQ ID NO:2.

The human 53010 sequence (see SEQ ID NO:1, as recited in Example 1), which is approximately 2158 nucleotides long including untranslated regions, contains a predicted methionine-initiated coding sequence of about 1746 nucleotides, including the termination codon. The coding sequence encodes a 581 amino acid protein (see SEQ ID NO:2, as recited in Example 1). The human 53010 protein of SEQ ID NO:2 includes an amino-terminal hydrophobic amino acid sequence, consistent with a signal sequence, of about 26 amino acids (from amino acid 1 to about amino acid 26 of SEQ ID NO:2), which upon cleavage results in the production of a mature protein form. The mature protein form is approximately 556 amino acid residues in length (from about amino acid 27 to amino acid 582 of SEQ ID NO:2).

Human 53010 contains the following regions or other structural features:

a carboxylesterase domain (PFAM Accession Number PF00135) located at about amino acid residues 44 to 545 of SEQ ID NO:2;

four predicted N-glycosylation sites (PS00001) from about amino acids 287–290, 369–372, 519–522, and 530–533 of SEQ ID NO:2;

six predicted Protein Kinase C phosphorylation sites (PS00005) at about amino acids 75–77, 310–312, 334–336, 368–370, 425–427, and 491–493 of SEQ ID NO:2;

eight predicted Casein Kinase II phosphorylation sites (PS00006) located at about amino acids 85–88, 161–164, 190–193, 289–292, 401–404, 408–411, 484–487, and 554–557 of SEQ ID NO:2;

eight predicted N-myristylation sites (PS00008) from about amino acids 4–9, 65–70, 153–158, 165–170, 220–225, 285–290, 367–372, and 505–510 of SEQ ID NO:2;

a predicted ATP/GTP-binding site motif A (P-loop) (PS00017) from about amino acids 23–30 of SEQ ID NO:2;

a predicted carboxylesterase type-B serine active site (PS00122) from about amino acids 219–234 of SEQ ID NO:2; and a predicted carboxylesterase type-B signature 2 (PS00941) from about amino acids 125–135 of SEQ ID NO:2.

For general information regarding PFAM identifiers, PS prefix and PF prefix domain identification numbers, refer to Sonnhammer et al. (1997) *Protein* 28:405–420 and http://www.psc.edu/general/software/packages/pfam/pfam.html.

The 53010 protein contains a significant number of structural characteristics in common with members of the carboxylesterase family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

Carboxylesterase family members are esterases that act on carboxylic esters. Based on the differential patterns of inhibition by organophosphates, carboxylesterases have been classified into three categories (A, B and C) (Myers, M. et al. (1988) *Mol. Biol. Evol.* 5(2):113–119). Carboxylesterase family members are characterized by a catalytic triad of amino acids: a serine, a glutamate or aspartate and a histidine. The 53010 polypeptides described herein bear homology to the carboxtlesterase type B family. The sequence around the active site of carboxtlesterase type B family members is well conserved and can be used to form the signature pattern F-[GR]-G-x(4)-[LIVM]-x-[LIV]-x-G-x-S-[STAG]-G (SEQ ID NO:5). In this pattern, S is the active site residue. A second signature pattern of carboxtlesterase type B family members is [ED]-D-C-L-[YT]-[LIV]-[DNS]-[LIV]-[LIVFYW]-x-[PQR] (SEQ ID NO:6), where C is involved in a disulfide bond.

A 53010 polypeptide can include a "carboxylesterase domain" or regions homologous with a "carboxylesterase domain".

As used herein, the term "carboxylesterase domain" includes an amino acid sequence of about 300 to 650 amino acid residues in length and having a bit score for the alignment of the sequence to the carboxylesterase domain (HMM) of at least 300. Preferably, a carboxylesterase domain includes at least about 400–600 amino acids, more preferably about 450–550 amino acid residues, or about 490–510 amino acids and has a bit score for the alignment of the sequence to the carboxylesterase domain (HMM) of at least 400, 450, 500, 540 or greater. The carboxylesterase domain (HMM) has been assigned the PFAM Accession Number PF00135 (http;//genome.wustl.edu/Pfam/.html). An alignment of the carboxylesterase domain (amino acids 44 to 545 of SEQ ID NO:2) of human 53010 with a consensus amino acid sequence (SEQ ID NO:4) derived from a hidden Markov model is depicted in FIG. 2.

In a preferred embodiment 53010 polypeptide or protein has a "carboxylesterase domain" or a region which includes at least about 400–600, more preferably about 450–550 or 490–510 amino acid residues and has at least about 50%, 60%, 70% 80% 90% 95%, 99%, or 100% homology with a "carboxylesterase domain," e.g., the carboxylesterase domain of human 53010 (e.g., residues 44 to 545 of SEQ ID NO:2).

To identify the presence of a "carboxylesterase" domain in a 53010 protein sequence, and make the determination that a polypeptide or protein of interest has a particular profile, the amino acid sequence of the protein can be searched against the Pfam database of HMMs (e.g., the Pfam database, release 2.1) using the default parameters (http://www.sanger.ac.uk/Software/Pfam/HMM_search). For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3):405–420 and a detailed description of HMMs can be found, for example, in Gribskov et al.(1990) *Meth. Enzymol.* 183:146–159; Gribskov et al.(1987) *Proc. Natl. Acad. Sci. USA* 84:4355–4358; Krogh et al.(1994) *J. Mol. Biol.* 235:1501–1531; and Stultz et al.(1993) *Protein Sci.* 2:305–314, the contents of which are incorporated herein by reference. A search was performed against the HMM database resulting in the identification of a "carboxylesterase" domain in the amino acid sequence of human 53010 at about residues 44 to 545 of SEQ ID NO:2 (see FIG. 2).

A 53010 molecule can include a carboxylesterase type-B serine active site. As used herein, the term "carboxylesterase type-B serine active site" includes an amino acid sequence of about 5–30, more preferably 10–20, most preferably 16 amino acids in length, which includes the consensus sequence F-[GR]-G-x(4)-[LIVM]-x-[LIV]-x-G-x-S-[STAG]-G (SEQ ID NO:5). Most preferably, the carboxylesterase type-B serine active site has a sequence at least 90%, 95%, 98%, or 100% identical to the amino acid sequence FGGDPSSVTIFGESAG (located at amino acids 219–234 of SEQ ID NO:2).

A 53010 molecule can include a carboxylesterase type-B signature 2. As used herein, the term "carboxylesterase type-B signature 2" includes an amino acid sequence of about 5–20, more preferably 8–15, most preferably 11 amino acids in length, which includes the consensus sequence [ED]-D-C-L-[YT]-[LIV]-[DNS]-[LIV]-[LIVFYW]-x-[PQR] (SEQ ID NO:6). Most preferably, the carboxylesterase type-B signature 2 has a sequence at least 90%, 95%, 98%, or 100% identical to the amino acid sequence EDCLYLNIYAP (located at amino acids 125–135 of SEQ ID NO:2).

A 53010 family member can include a carboxylesterase domain; a carboxylesterase type-B serine active site; and a carboxylesterase type-B signature 2.

Furthermore, a 53010 family member can include at least one, two, three, and preferably four N-glycosylation sites (PS00001); at least one, two, three, four, five, and preferably six protein kinase C phosphorylation sites (PS00005); at least one, two, three, four, five, six, seven, and preferably eight predicted casein kinase II phosphorylation sites (PS00006); at least one, two, three, four, five, six, seven, and preferably eight predicted N-myristylation sites (PS00008); and at least one ATP/GTP-binding site motif A (PS00017);

As the 53010 polypeptides of the invention may modulate 53010-mediated activities, they may be useful as of for developing novel diagnostic and therapeutic agents for 53010-mediated or related disorders, as described below.

As used herein, a "53010 activity", "biological activity of 53010" or "functional activity of 53010", refers to an activity exerted by a 53010 protein, polypeptide or nucleic acid molecule. For example, a 53010 activity can be an activity exerted by 53010 in a physiological milieu on, e.g., a 53010-responsive cell or on a 53010 substrate, e.g., a protein substrate. A 53010 activity can be determined in vivo or in vitro. In one embodiment, a 53010 activity is a direct activity, such as an association with a 53010 target molecule. A "target molecule" or "binding partner" is a molecule with which a 53010 protein binds or interacts in nature. In an exemplary embodiment, 53010 is an enzyme that catalyzes the hydrolysis of carboxylic esters.

A 53010 activity can also be an indirect activity, e.g., a cellular signaling activity mediated by interaction of the 53010 protein with a 53010 receptor. The features of the 53010 molecules of the present invention can provide similar biological activities as carboxylesterase family members. For example, the 53010 proteins of the present invention can have one or more of the following activities: (1) the ability to catalyze the hydrolysis of carboxylic esters; (2) the ability to modulate cell—cell recognition events, e.g., adhesion or attachment; (3) the ability to interact with a cell surface protein, an extracellular protein, or an extracellular component; (4) the ability catalyze the posttranslational conversion of glutamic acid to gamma-carboxyglutamic acid; (5) the ability to modulate blood coagulation; (6) the ability to modulate cell migration; (7) the ability to modulate proliferation and/or differentiation of a cell (e.g., a neural or a cancer cell); (8) the ability to modulate embryonic development and differentiation; (9) the ability to modulate tissue maintenance; (10) the ability to modulate neural development; (11) the ability to bind a divalent cation, e.g., $Zn^{2+}$, $Mg^{2+}$, $Cd^{2+}$, $Mn^{2+}$ and/or preferably a $Ca^{2+}$ ion; or (12) the ability to modulate pain or inflammation response.

Thus, the 53010 molecules can act as novel diagnostic targets and therapeutic agents for controlling disorders involving aberrant or deficient hydrolysis of carboxylic esters.

53010 is highly expressed in the central and peripheral nervous system. For example, Tables 1–3 show that 53010 mRNA is expressed at high levels, relative to other tissues tested, in the brain, spinal cord, and dorsal root ganglion. The rat orthologue of 53010 was found to be expressed at low levels only in the nervous system tissues. In situ hybridization experiments with a human 53010 probe showed expression of 53010 in a subpopulation of neurons in the human thalamus and low levels of expression in monkey hippocampus (CA layers), spinal cord, and dorsal root ganglion. Low levels of 53010 expression were also detected in human cortex, and higher levels were observed in subpopulation of thalamic nuclei. In rat, in situ hybridization experiments with a rat 53010 probe detected expression in the brain restricted to the ventro posterior, ventrolateral and postero ventral nuclei of the thalamus. These are the nuclei that received information from the spinal cord and the dorsal column nuclei. Low levels of expression were observed in the spinal cord. The rodent 53010 gene was found to be expressed at low levels in the dorsal root ganglion, except in a very few small diameter neurons that express much higher levels.

Animal models of pain response include, but are not limited to: axotomy, the cutting or severing of an axon (Gustafsson et al. (2000) Neuroreport 11:3345–48); chronic constriction injury (CCI), also known as the Bennett model, a model of neuropathic pain which involves ligation of the sciatic nerve in rodents, e.g., rats (Eaton et al. (2000) Cell Transplant. 9:637–56); and intraplantar complete Freund's adjuvant (CFA) injection as a model of arthritic pain (Fraser et al. (2000) Br. J. Pharmacol. 129:1668–72). Other animal models of pain response are described in, e.g., ILAR Journal (1999) Volume 40, Number 3 (entire issue). 53010 expression was shown to be slightly upregulated in some pain response models (see Tables 4 and 5).

Carboxylesterases are regulators of lipid metabolism and have a broad specificity. They catalyze the reactions of acylglycerol lipases (that hydrolyze 2-AG and DAG into arachidonic acid). Carboxylesterases also catalyze amidase reactions (inactivating endogenous cannabinoids) and lysophospholipase reactions (the enzyme that produces lysophosphatidic acid, a pain-inducing factor that acts directly on the afferent terminal). Carboxylesterase inhibitors can increase the levels of 2-AG (an endogenous cannabinoid).

As the 53010 mRNA is expressed in the central and peripheral nervous system (e.g., brain, spinal cord, and dorsal root ganglion (DRG)) of primates, e.g., human and monkeys, and its expression is regulated expression in some rodent pain models, 53010 molecules can act as novel diagnostic targets and therapeutic agents for controlling neurological disorders, such as pain-related disorders.

Examples of pain conditions include, but are not limited to, pain elicited during various forms of tissue injury, e.g., inflammation, infection, and ischemia; pain associated with musculoskeletal disorders, e.g., joint pain, or arthritis; tooth pain; headaches, e.g., migrane; pain associated with surgery; pain related to inflammation, e.g., irritable bowel syndrome; chest pain; or hyperalgesia, e.g., excessive sensitivity to pain (described in, for example, Fields (1987) Pain, New York:McGraw-Hill). Other examples of pain disorders or pain syndromes include, but are not limited to, complex regional pain syndrome (CRPS), reflex sympathetic dystrophy (RSD), causalgia, neuralgia, central pain and dysesthesia syndrome, carotidynia, neurogenic pain, refractory cervicobrachial pain syndrome, myofascial pain syndrome, craniomandibular pain dysfunction syndrome, chronic idiopathic pain syndrome, Costen's pain-dysfunction, acute chest pain syndrome, nonulcer dyspepsia, interstitial cystitis, gynecologic pain syndrome, patellofemoral pain syndrome, anterior knee pain syndrome, recurrent abdominal pain in children, colic, low back pain syndrome, neuropathic pain, phantom pain from amputation, phantom tooth pain, or pain asymbolia (the inability to feel pain). Other examples of pain conditions include pain induced by parturition, or post partum pain.

Agents that modulate 53010 polypeptide or nucleic acid activity or expression can be used to treat pain elicited by any medical condition. A subject receiving the treatment can be additionally treated with a second agent, e.g., an anti-inflammatory agent, an antibiotic, or a chemotherapeutic agent, to further ameliorate the condition.

The 53010 molecules can also act as novel diagnostic targets and therapeutic agents controlling pain caused by other disorders, e.g., cancer, e.g., prostate cancer.

The molecules of the invention may also serve as diagnostic and therapeutic targets for neurological disorders in addition to the ones described above. Examples of such neurological disorders include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia;

perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, *Herpes simplex* virus Type 1, *Herpes simplex* virus Type 2, *Varicalla-zoster* virus (*Herpes zoster*), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

The 53010 protein, fragments thereof, and derivatives and other variants of the sequence in SEQ ID NO:2 thereof are collectively referred to as "polypeptides or proteins of the invention" or "53010 polypeptides or proteins". Nucleic acid molecules encoding such polypeptides or proteins are collectively referred to as "nucleic acids of the invention" or "53010 nucleic acids." 53010 molecules refer to 53010 nucleic acids, polypeptides, and antibodies.

As used herein, the term "nucleic acid molecule" includes DNA molecules (e.g., a cDNA or genomic DNA), RNA molecules (e.g., an mRNA) and analogs of the DNA or RNA. A DNA or RNA analog can be synthesized from nucleotide analogs. The nucleic acid molecule can be single-stranded or double-stranded, but preferably is double-stranded DNA.

The term "isolated nucleic acid molecule" or "purified nucleic acid molecule" includes nucleic acid molecules that are separated from other nucleic acid molecules present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1–6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2× SSC, 0.1% SDS at least at 50° C. (the temperature of the washes can be increased to 55° C. for low stringency conditions); 2) medium stringency hybridization conditions in 6× SSC at about 45° C., followed by one or more washes in 0.2× SSC, 0.1% SDS at 60° C.; 3) high stringency hybridization conditions in 6× SSC at about 45° C., followed by one or more washes in 0.2× SSC, 0.1% SDS at 65° C.; and preferably 4) very high stringency hybridization conditions are 0.5M sodium phosphate, 7% SDS at 65° C., followed by one or more washes at 0.2× SSC, 1% SDS at 65° C. Very high stringency conditions (4) are the preferred conditions and the ones that should be used unless otherwise specified.

Preferably, an isolated nucleic acid molecule of the invention that hybridizes under a stringency condition described herein to the sequence of SEQ ID NO:1 or SEQ ID NO:3, corresponds to a naturally-occurring nucleic acid molecule.

As used herein, a "naturally-occurring" nucleic acid molecule refers to an RNA or DNA molecule having a nucleotide sequence that occurs in nature. For example a naturally occurring nucleic acid molecule can encode a natural protein. As used herein, the terms "gene" and "recombinant gene" refer to nucleic acid molecules which include at least an open reading frame encoding a 53010 protein. The gene can optionally further include non-coding sequences, e.g., regulatory sequences and introns. Preferably, a gene encodes a mammalian 53010 protein or derivative thereof.

An "isolated" or "purified" polypeptide or protein is substantially free of cellular material or other contaminating proteins from the cell or tissue source from which the protein is derived, or substantially free from chemical precursors or other chemicals when chemically synthesized. "Substantially free" means that a preparation of 53010 protein is at least 10% pure. In a preferred embodiment, the preparation of 53010 protein has less than about 30%, 20%, 10% and more preferably 5% (by dry weight), of non-53010 protein (also referred to herein as a "contaminating protein"), or of chemical precursors or non-53010 chemicals. When the 53010 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 53010 without abolishing or substantially altering a 53010 activity. Preferably the alteration does not substantially alter the 53010 activity, e.g., the activity is at least 20%, 40%, 60%, 70% or 80% of wild-type. An "essential" amino acid residue is a residue that, when altered from the wild-type sequence of 53010, results in abolishing a 53010 activity such that less than 20% of the wild-type activity is present. For example, conserved amino acid residues in 53010 are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 53010 protein is preferably replaced with another amino acid residue from the same side chain family. Alternatively, in another embodiment, mutations can be introduced randomly along all or part of a 53010 coding sequence, such as by saturation mutagenesis, and the resultant mutants can be screened for 53010 biological activity to identify mutants that retain activity. Following mutagenesis of SEQ ID NO:1 or SEQ ID NO:3, the encoded protein can be expressed recombinantly and the activity of the protein can be determined.

As used herein, a "biologically active portion" of a 53010 protein includes a fragment of a 53010 protein which participates in an interaction, e.g., an intramolecular or an inter-molecular interaction. An inter-molecular interaction can be a specific binding interaction or an enzymatic interaction (e.g., the interaction can be transient and a covalent bond is formed or broken). An inter-molecular interaction can be between a 53010 molecule and a non-53010 molecule or between a first 53010 molecule and a second 53010 molecule (e.g., a dimerization interaction). Biologically active portions of a 53010 protein include peptides comprising amino acid sequences sufficiently homologous to or derived from the amino acid sequence of the 53010 protein, e.g., the amino acid sequence shown in SEQ ID NO:2, which include less amino acids than the full length 53010 proteins, and exhibit at least one activity of a 53010 protein. Typically, biologically active portions comprise a domain or motif with at least one activity of the 53010 protein, e.g., the ability to catalyze the hydrolysis of carboxylic esters. A biologically active portion of a 53010 protein can be a polypeptide which is, for example, 10, 25, 50, 100, 200 or more amino acids in length. Biologically active portions of a 53010 protein can be used as targets for developing agents which modulate a 53010 mediated activity, e.g., the ability to catalyze the hydrolysis of carboxylic esters.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444–453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11–17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to 53010 nucleic acid molecules of the invention. BLAST protein searches can be performed with the XBLAST program, score=50, wordlength=3 to obtain amino acid sequences homologous to 53010 protein molecules of the invention. To obtain gapped alignments for comparison purposes, Gapped BLAST can be utilized as described in Altschul et al., (1997) *Nucleic Acids Res.* 25:3389–3402. When utilizing BLAST and Gapped BLAST programs, the default parameters of the respective programs (e.g., XBLAST and NBLAST) can be used. See http://www.ncbi.nlm.nih.gov.

Particularly preferred 53010 polypeptides of the present invention have an amino acid sequence substantially identical to the amino acid sequence of SEQ ID NO:2. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 60%, or 65% identity, likely 75% identity, more likely 85%, 90%. 91%, 92%, 93%, 94%, 95%, 96%, 97%, 98% or 99% identity to SEQ ID NO:2 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 60%, or 65% identity, likely 75% identity, more likely 85%, 90%. 91%, 92%, 93%, 94%, 95%, 96%, 97%, 98% or 99% identity to SEQ ID NO:1 or 3 are termed substantially identical. "Misexpression or aberrant expression", as used herein, refers to a non-wildtype pattern of gene expression at the RNA or protein level. It includes: expression at non-wild type levels, i.e., over- or under-expression; a pattern of expression that differs from wild type in terms of the time or stage at which the gene is expressed, e.g., increased or decreased expression (as compared with wild type) at a predetermined developmental period or stage; a pattern of expression that differs from wild type in terms of altered, e.g., increased or decreased, expression (as compared with wild type) in a predetermined cell type or tissue type; a pattern of expression that differs from wild type in terms of the splicing size, translated amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject," as used herein, refers to human and non-human animals. The term "non-human animals" of the invention includes all vertebrates, e.g., mammals, such as non-human primates (particularly higher primates), sheep, dog, rodent (e.g., mouse or rat), guinea pig, goat, pig, cat, rabbits, cow, and non-mammals, such as chickens, amphibians, reptiles, etc. In a preferred embodiment, the subject is a human. In another embodiment, the subject is an experimental animal or animal suitable as a disease model.

A "purified preparation of cells", as used herein, refers to an in vitro preparation of cells. In the case cells from multicellular organisms (e.g., plants and animals), a purified preparation of cells is a subset of cells obtained from the organism, not the entire intact organism. In the case of unicellular microorganisms (e.g., cultured cells and microbial cells), it consists of a preparation of at least 10% and more preferably 50% of the subject cells.

Various aspects of the invention are described in further detail below.

Isolated Nucleic Acid Molecules

In one aspect, the invention provides, an isolated or purified, nucleic acid molecule that encodes a 53010 polypeptide described herein, e.g., a full-length 53010 protein or a fragment thereof, e.g., a biologically active portion of 53010 protein. Also included is a nucleic acid fragment suitable for use as a hybridization probe, which can be used, e.g., to identify a nucleic acid molecule encoding a polypeptide of the invention, 53010 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:1, or a portion of any of these nucleotide sequences. In one embodiment, the nucleic acid molecule includes sequences encoding the human 53010 protein (i.e., "the coding region" of SEQ ID NO:1, as shown in SEQ ID NO:3), as well as 5' untranslated sequences. Alternatively, the nucleic acid molecule can include only the coding region of SEQ ID NO:1 (e.g., SEQ ID NO:3) and, e.g., no flanking sequences which normally accompany the subject sequence. In another embodiment, the nucleic acid molecule encodes a sequence corresponding to a fragment of the protein from about amino acid 44 to 545.

In another embodiment, an isolated nucleic acid molecule of the invention includes a nucleic acid molecule which is a complement, e.g., a full complement, of the nucleotide sequence shown in SEQ ID NO:1 or SEQ ID NO:3, or a portion of any of these nucleotide sequences. In other embodiments, the nucleic acid molecule of the invention is sufficiently complementary to the nucleotide sequence shown in SEQ ID NO:1 or SEQ ID NO:3, such that it can hybridize (e.g., under a stringency condition described herein) to the nucleotide sequence shown in SEQ ID NO:1 or 3, thereby forming a stable duplex.

In one embodiment, an isolated nucleic acid molecule of the present invention includes a nucleotide sequence which is at least about: 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO:1 or SEQ ID NO:3, or a portion, preferably of the same length, of any of these nucleotide sequences.

53010 Nucleic Acid Fragments

A nucleic acid molecule of the invention can include only a portion of the nucleic acid sequence of SEQ ID NO:1 or 3. For example, such a nucleic acid molecule can include a fragment which can be used as a probe or primer or a fragment encoding a portion of a 53010 protein, e.g., an immunogenic or biologically active portion of a 53010 protein. A fragment can comprise those nucleotides of SEQ ID NO:1, which encode a carboxylesterase domain of human 53010. The nucleotide sequence determined from the cloning of the 53010 gene allows for the generation of probes and primers designed for use in identifying and/or cloning other 53010 family members, or fragments thereof, as well as 53010 homologues, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 50, 100, 150, 200, 250, 300, 350, 400, 450, 500, or 550 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, a 53010 nucleic acid fragment can include a sequence corresponding to a carboxylesterase domain.

53010 probes and primers are provided. Typically a probe/primer is an isolated or purified oligonucleotide. The oligonucleotide typically includes a region of nucleotide sequence that hybridizes under a stringency condition described herein to at least about 7, 12 or 15, preferably about 20 or 25, more preferably about 30, 35, 40, 45, 50, 55, 60, 65, or 75 consecutive nucleotides of a sense or antisense sequence of SEQ ID NO: 1 or SEQ ID NO:3, or of a naturally occurring allelic variant or mutant of SEQ ID NO:1 or SEQ ID NO:3. Preferably, an oligonucleotide is less than about 200, 150, 120, or 100 nucleotides in length.

In one embodiment, the probe or primer is attached to a solid support, e.g., a solid support described herein.

One exemplary kit of primers includes a forward primer that anneals to the coding strand and a reverse primer that anneals to the non-coding strand. The forward primer can anneal to the start codon, e.g., the nucleic acid sequence encoding amino acid residue 1 of SEQ ID NO:2. The reverse primer can anneal to the ultimate codon, e.g., the codon immediately before the stop codon, e.g., the codon encoding amino acid residue 581 of SEQ ID NO:2. In a preferred embodiment, the annealing temperatures of the forward and reverse primers differ by no more than 5, 4, 3, or 2° C.

In a preferred embodiment the nucleic acid is a probe which is at least 10, 12, 15, 18, 20 and less than 200, more preferably less than 100, or less than 50, nucleotides in length. It should be identical, or differ by 1, or 2, or less than 5 or 10 nucleotides, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes: a carboxylesterase domain (e.g., amino acids 44 to 545 of SEQ ID NO:2); a carboxylesterase type-B serine active site (e.g., amino acids 125–135 of SEQ ID NO:2); or carboxylesterase type-B signature 2 (e.g., amino acids 125–135 of SEQ ID NO:2).

In another embodiment a set of primers is provided, e.g., primers suitable for use in a PCR, which can be used to amplify a selected region of a 53010 sequence, e.g., a domain, region, site or other sequence described herein. The primers should be at least 5, 10, or 50 base pairs in length and less than 100, or less than 200, base pairs in length. The primers should be identical, or differs by one base from a sequence disclosed herein or from a naturally occurring variant. For example, primers suitable for amplifying all or a portion of any of the following regions are provided: a carboxylesterase domain (e.g., amino acids 44 to 545 of SEQ ID NO:2); a carboxylesterase type-B serine active site (e.g., amino acids 125–135 of SEQ ID NO:2); or carboxylesterase type-B signature 2 (e.g., amino acids 125–135 of SEQ ID NO:2).

A nucleic acid fragment can encode an epitope bearing region of a polypeptide described herein.

A nucleic acid fragment encoding a "biologically active portion of a 53010 polypeptide" can be prepared by isolating a portion of the nucleotide sequence of SEQ ID NO: 1 or 3, which encodes a polypeptide having a 53010 biological activity (e.g., the biological activities of the 53010 proteins are described herein), expressing the encoded portion of the 53010 protein (e.g., by recombinant expression in vitro) and assessing the activity of the encoded portion of the 53010 protein. For example, a nucleic acid fragment encoding a biologically active portion of 53010 includes a carboxylesterase domain, e.g., amino acid residues about 44 to 545 of SEQ ID NO:2. A nucleic acid fragment encoding a biologically active portion of a 53010 polypeptide, may comprise a nucleotide sequence which is greater than 300 or more nucleotides in length.

In preferred embodiments, a nucleic acid includes a nucleotide sequence which is about 300, 400, 500, 600, 700, 800, 900, 1000, 1100, 1200, 1300 or more nucleotides in length and hybridizes under a stringency condition described herein to a nucleic acid molecule of SEQ ID NO:1, or SEQ ID NO:3.

53010 Nucleic Acid Variants

The invention further encompasses nucleic acid molecules that differ from the nucleotide sequence shown in SEQ ID NO:1 or SEQ ID NO:3. Such differences can be due to degeneracy of the genetic code (and result in a nucleic acid which encodes the same 53010 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:2. If alignment is needed for this comparison the sequences should be aligned for maximum homology. The encoded protein can differ by no more than 5, 4, 3, 2, or 1 amino acid. "Looped" out sequences from deletions or insertions, or mismatches, are considered differences.

Nucleic acids of the inventor can be chosen for having codons, which are preferred, or non-preferred, for a particular expression system. E.g., the nucleic acid can be one in which at least one codon, at preferably at least 10%, or 20% of the codons has been altered such that the sequence is optimized for expression in E. coli, yeast, human, insect, or CHO cells.

Nucleic acid variants can be naturally occurring, such as allelic variants (same locus), homologs (different locus), and orthologs (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO: 1 or 3, e.g., as follows: by at least one but less than 10, 20, 30, or 40 nucleotides; at least one but less than 1%, 5%, 10% or 20% of the nucleotides in the subject nucleic acid. The nucleic acid can differ by no more than 5, 4, 3, 2, or 1 nucleotide. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70–75%, more typically at least about 80–85%, and most typically at least about 90–95% or more identical to the nucleotide sequence shown in SEQ ID NO:2 or a fragment of this sequence. Such nucleic acid molecules can readily be identified as being able to hybridize under a stringency condition described herein, to the nucleotide sequence shown in SEQ ID NO 2 or a fragment of the sequence. Nucleic acid molecules corresponding to orthologs, homologs, and allelic variants of the 53010 cDNAs of the invention can further be isolated by mapping to the same chromosome or locus as the 53010 gene.

Preferred variants include those that are correlated with the ability to catalyze the hydrolysis of carboxylic esters.

Allelic variants of 53010, e.g., human 53010, include both functional and non-functional proteins. Functional allelic variants are naturally occurring amino acid sequence variants of the 53010 protein within a population that maintain the ability to catalyze the hydrolysis of carboxylic esters. Functional allelic variants will typically contain only conservative substitution of one or more amino acids of SEQ ID NO:2, or substitution, deletion or insertion of non-critical residues in non-critical regions of the protein. Non-functional allelic variants are naturally-occurring amino acid sequence variants of the 53010, e.g., human 53010, protein within a population that do not have the ability to catalyze the hydrolysis of carboxylic esters. Non-functional allelic variants will typically contain a non-conservative substitution, a deletion, or insertion, or premature truncation of the amino acid sequence of SEQ ID NO:2, or a substitution, insertion, or deletion in critical residues or critical regions of the protein.

Moreover, nucleic acid molecules encoding other 53010 family members and, thus, which have a nucleotide sequence which differs from the 53010 sequences of SEQ ID NO:1 or SEQ ID NO:3 are intended to be within the scope of the invention.

Antisense Nucleic Acid Molecules, Ribozymes and Modified 53010 Nucleic Acid Molecules In another aspect, the invention features, an isolated nucleic acid molecule which is antisense to 53010. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire 53010 coding strand, or to only a portion thereof (e.g., the coding region of human 53010 corresponding to SEQ ID NO:3). In another embodiment, the antisense nucleic acid molecule is antisense to a "noncoding region" of the coding strand of a nucleotide sequence encoding 53010 (e.g., the 5' and 3' untranslated regions).

An antisense nucleic acid can be designed such that it is complementary to the entire coding region of 53010 mRNA, but more preferably is an oligonucleotide which is antisense to only a portion of the coding or noncoding region of 53010 mRNA. For example, the antisense oligonucleotide can be complementary to the region surrounding the translation start site of 53010 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 53010 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) (*Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. A ribozyme having specificity for a 53010-encoding nucleic acid can include one or more sequences complementary to the nucleotide sequence of a 53010 cDNA disclosed herein (i.e., SEQ ID NO:1 or SEQ ID NO:3), and a sequence having known catalytic sequence responsible for mRNA cleavage (see U.S. Pat. No. 5,093, 246 or Haselhoff and Gerlach (1988) *Nature* 334:585–591). For example, a derivative of a Tetrahymena L-19 IVS RNA can be constructed in which the nucleotide sequence of the active site is complementary to the nucleotide sequence to be cleaved in a 53010-encoding mRNA. See, e.g., Cech et al. U.S. Pat. No. 4,987,071; and Cech et al. U.S. Pat. No. 5,116,742. Alternatively, 53010 mRNA can be used to select a catalytic RNA having a specific ribonuclease activity from a pool of RNA molecules. See, e.g., Bartel, D. and Szostal J. W. (1993) *Science* 261:1411–1418.

53010 gene expression can be inhibited by targeting nucleotide sequences complementary to the regulatory region of the 53010 (e.g., the 53010 promoter and/or enhancers) to form triple helical structures that prevent transcription of the 53010 gene in target cells. See generally, Helene, C. (1991) *Anticancer Drug Des.* 6:569–84; Helene, C. i (1992) *Ann. N. Y Acad. Sci.* 660:27–36; and Maher, L. J. (1992) *Bioassays* 14:807–15. The potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or calorimetric.

A 53010 nucleic acid molecule can be modified at the base moiety, sugar moiety or phosphate backbone to improve, e.g., the stability, hybridization, or solubility of the molecule. For non-limiting examples of synthetic oligonucleotides with modifications see Toulmé (2001) *Nature Biotech.* 19:17 and Faria et al. (2001) *Nature Biotech.* 19:40–44. Such phosphoramidite oligonucleotides can be effective antisense agents.

For example, the deoxyribose phosphate backbone of the nucleic acid molecules can be modified to generate peptide nucleic acids (see Hyrup B. et al. (1996) *Bioorganic & Medicinal Chemistry* 4: 5–23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra and Perry-O'Keefe et al. *Proc. Natl. Acad. Sci.* 93: 14670–675.

PNAs of 53010 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 53010 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. et al. (1996) supra)); or as probes or primers for DNA sequencing or hybridization (Hyrup B. et al. (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (see, e.g., Krol et al. (1988) *Bio-Techniques* 6:958–976) or intercalating agents. (see, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 53010 nucleic acid of the invention, two complementary regions one having a fluorophore and one a quencher such that the molecular beacon is useful for quantitating the presence of the 53010 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated 53010 Polypeptides

In another aspect, the invention features, an isolated 53010 protein, or fragment, e.g., a biologically active portion, for use as immunogens or antigens to raise or test (or more generally to bind) anti-53010 antibodies. 53010 protein can be isolated from cells or tissue sources using standard protein purification techniques. 53010 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when expressed the polypeptide is expressed in a native cell, or in systems which result in the alteration or omission of post-translational modifications, e.g., glycosylation or cleavage, present when expressed in a native cell.

In a preferred embodiment, a 53010 polypeptide has one or more of the following characteristics:

(i) it has the ability to catalyze the hydrolysis of carboxylic esters;

(ii) it has a molecular weight, e.g., a deduced molecular weight, preferably ignoring any contribution of post translational modifications, amino acid composition or other physical characteristic of a 53010 polypeptide, e.g., a polypeptide of SEQ ID NO:2;

(iii) it has an overall sequence similarity of at least 60%, more preferably at least 70, 80, 90, or 95%, with a 53010 polypeptide, e.g., a polypeptide of SEQ ID NO:2;

(iv) it has a carboxylesterase domain which is preferably about 70%, 80%, 90% or 95% with amino acid residues about 44 to 545 of SEQ ID NO:2;

(v) it has a carboxylesterase type-B serine active site which is preferably about 70%, 80%, 90% or 95% with amino acid residues about 219–234 of SEQ ID NO:2;

(vi) it has a carboxylesterase type-B signature 2 which is preferably about 70%, 80%, 90% or 95% with amino acid residues about 125 to 135 of SEQ ID NO:2; or (vii) it has at least one, preferably five, and most preferably six of the cysteines found in the amino acid sequence of the native protein.

In a preferred embodiment the 53010 protein, or fragment thereof, differs from the corresponding sequence in SEQ ID NO:2. In one embodiment it differs by at least one but by less than 15, 10 or 5 amino acid residues. In another it differs from the corresponding sequence in SEQ ID NO:2 by at least one residue but less than 20%, 15%, 10% or 5% of the residues in it differ from the corresponding sequence in SEQ ID NO:2. (If this comparison requires alignment the sequences should be aligned for maximum homology. "Looped" out sequences from deletions or insertions, or mismatches, are considered differences.) The differences are, preferably, differences or changes at a non essential residue or a conservative substitution. In a preferred embodiment the differences are not in the carboxylesterase domain of from about amino acid 44 to 545 of SEQ ID NO:2. In another preferred embodiment one or more differences are in the carboxylesterase domain of from about amino acid 44 to 545 of SEQ ID NO:2.

Other embodiments include a protein that contain one or more changes in amino acid sequence, e.g., a change in an amino acid residue which is not essential for activity. Such 53010 proteins differ in amino acid sequence from SEQ ID NO:2, yet retain biological activity.

In one embodiment, the protein includes an amino acid sequence at least about 50%, 55%, 60%, 65%, 70%, 75%, 80%, 85%, 90%, 95%, 98% or more homologous to SEQ ID NO:2.

A 53010 protein or fragment is provided which varies from the sequence of SEQ ID NO.2 in regions defined by amino acids about 1 to 138 by at least one but by less than 15, 10 or 5 amino acid residues in the protein or fragment but which does not differ from SEQ ID NO.2 in regions defined by amino acids about 44 to 545. (If this comparison requires alignment the sequences should be aligned for maximum homology. "Looped" out sequences from deletions or insertions, or mismatches, are considered differences.) In some embodiments the difference is at a non-essential residue or is a conservative substitution, while in others the difference is at an essential residue or is a non-conservative substitution.

In one embodiment, a biologically active portion of a 53010 protein includes a carboxylesterase domain. Moreover, other biologically active portions, in which other regions of the protein are deleted, can be prepared by recombinant techniques and evaluated for one or more of the functional activities of a native 53010 protein.

In a preferred embodiment, the 53010 protein has an amino acid sequence shown in SEQ ID NO:2. In other embodiments, the 53010 protein is substantially identical to SEQ ID NO:2. In yet another embodiment, the 53010 protein is substantially identical to SEQ ID NO:2 and retains the functional activity of the protein of SEQ ID NO:2, as described in detail in the subsections above.

53010 Chimeric or Fusion Proteins

In another aspect, the invention provides 53010 chimeric or fusion proteins. As used herein, a 53010 "chimeric protein" or "fusion protein" includes a 53010 polypeptide linked to a non-53010 polypeptide. A "non-53010 polypeptide" refers to a polypeptide having an amino acid sequence corresponding to a protein which is not substantially homologous to the 53010 protein, e.g., a protein which is different from the 53010 protein and which is derived from the same or a different organism. The 53010 polypeptide of the fusion protein can correspond to all or a portion e.g., a fragment described herein of a 53010 amino acid sequence. In a preferred embodiment, a 53010 fusion protein includes at least one (or two) biologically active portion of a 53010 protein. The non-53010 polypeptide can be fused to the N-terminus or C-terminus of the 53010 polypeptide.

The fusion protein can include a moiety which has a high affinity for a ligand. For example, the fusion protein can be a GST-53010 fusion protein in which the 53010 sequences are fused to the C-terminus of the GST sequences. Such fusion proteins can facilitate the purification of recombinant 53010. Alternatively, the fusion protein can be a 53010 protein containing a heterologous signal sequence at its N-terminus. In certain host cells (e.g., mammalian host cells), expression and/or secretion of 53010 can be increased through use of a heterologous signal sequence.

Fusion proteins can include all or a part of a serum protein, e.g., an IgG constant region, or human serum albumin.

The 53010 fusion proteins of the invention can be incorporated into pharmaceutical compositions and administered to a subject in vivo. The 53010 fusion proteins can be used to affect the bioavailability of a 53010 substrate. 53010 fusion proteins may be useful therapeutically for the treatment of disorders caused by, for example, (i) aberrant modification or mutation of a gene encoding a 53010 protein; (ii) mis-regulation of the 53010 gene; and (iii) aberrant post-translational modification of a 53010 protein.

Moreover, the 53010-fusion proteins of the invention can be used as immunogens to produce anti-53010 antibodies in a subject, to purify 53010 ligands and in screening assays to identify molecules which inhibit the interaction of 53010 with a 53010 substrate.

Expression vectors are commercially available that already encode a fusion moiety (e.g., a GST polypeptide). A 53010-encoding nucleic acid can be cloned into such an expression vector such that the fusion moiety is linked in-frame to the 53010 protein.

Variants of 53010 Proteins

In another aspect, the invention also features a variant of a 53010 polypeptide, e.g., which functions as an agonist (mimetics) or as an antagonist. Variants of the 53010 proteins can be generated by mutagenesis, e.g., discrete point mutation, the insertion or deletion of sequences or the truncation of a 53010 protein. An agonist of the 53010 proteins can retain substantially the same, or a subset, of the biological activities of the naturally occurring form of a 53010 protein. An antagonist of a 53010 protein can inhibit one or more of the activities of the naturally occurring form of the 53010 protein by, for example, competitively modulating a 53010-mediated activity of a 53010 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 53010 protein.

Variants of a 53010 protein can be identified by screening combinatorial libraries of mutants, e.g., truncation mutants, of a 53010 protein for agonist or antagonist activity.

Libraries of fragments e.g., N terminal, C terminal, or internal fragments, of a 53010 protein coding sequence can be used to generate a variegated population of fragments for screening and subsequent selection of variants of a 53010 protein. Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of 53010 proteins. Recursive ensemble mutagenesis (REM), a new technique which enhances the frequency of functional mutants in the libraries, can be used in combination with the screening assays to identify 53010 variants (Arkin and Yourvan (1992) *Proc. Natl. Acad. Sci. USA* 89:7811–7815; Delgrave et al. (1993) *Protein Engineering* 6:327–331).

Cell based assays can be exploited to analyze a variegated 53010 library. For example, a library of expression vectors can be transfected into a cell line, e.g., a cell line, which ordinarily responds to 53010 in a substrate-dependent manner. The transfected cells are then contacted with 53010 and the effect of the expression of the mutant on signaling by the 53010 substrate can be detected, e.g., by measuring carboxylesterase activity. Plasmid DNA can then be recovered from the cells which score for inhibition, or alternatively, potentiation of signaling by the 53010 substrate, and the individual clones further characterized.

In another aspect, the invention features a method of making a 53010 polypeptide, e.g., a peptide having a non-wild type activity, e.g., an antagonist, agonist, or super agonist of a naturally occurring 53010 polypeptide, e.g., a naturally occurring 53010 polypeptide. The method includes: altering the sequence of a 53010 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a 53010 polypeptide a biological activity of a naturally occurring 53010 polypeptide. The method includes: altering the sequence, e.g., by substitution or deletion of one or more residues, of a 53010 polypeptide, e.g., altering the sequence of a non-conserved region, or a domain or residue described herein, and testing the altered polypeptide for the desired activity.

Anti-53010 Antibodies

In another aspect, the invention provides an anti-53010 antibody, or a fragment thereof (e.g., an antigen-binding fragment thereof). The term "antibody" as used herein refers to an immunoglobulin molecule or immunologically active portion thereof, i.e., an antigen-binding portion. As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of Proteins of Immunological Interest, Fifth Edition,* U.S. Department of Health and Human Services, NIH Publication No. 91-3242, and Chothia, C. et al. (1987) J. Mol. Biol. 196:901–917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4.

The anti-53010 antibody can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 KDa or 214 amino acids) are encoded by a variable region gene at the NH2-terminus (about 110 amino acids) and a kappa or lambda constant region gene at the COOH—terminus. Full-length immunoglobulin "heavy chains" (about 50 KDa or 446 amino acids), are similarly encoded by a variable region gene (about 116 amino acids) and one of the other aforementioned constant region genes, e.g., gamma (encoding about 330 amino acids).

The term "antigen-binding fragment" of an antibody (or simply "antibody portion," or "fragment"), as used herein, refers to one or more fragments of a full-length antibody that retain the ability to specifically bind to the antigen, e.g., 53010 polypeptide or fragment thereof. Examples of antigen-binding fragments of the anti-53010 antibody include, but are not limited to: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544–546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423–426; and Huston et al. (1988) *Proc. Natl. Acad. Sci. USA* 85:5879–5883). Such single chain antibodies are also encompassed within the term "antigen-binding fragment" of an antibody. These antibody fragments are obtained using conventional techniques known to those with skill in the art, and the fragments are screened for utility in the same manner as are intact antibodies.

The anti-53010 antibody can be a polyclonal or a monoclonal antibody. In other embodiments, the antibody can be recombinantly produced, e.g., produced by phage display or by combinatorial methods.

Phage display and combinatorial methods for generating anti-53010 antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370–1372; Hay et al. (1992) *Hum Antibod Hybridomas* 3:81–85; Huse et al. (1989) *Science* 246:1275–1281; Griffths et al. (1993) *EMBO J* 12:725–734; Hawkins et al. (1992) *J Mol Biol* 226:889–896; Clackson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc Acid Res* 19:4133–4137; and Barbas et al. (1991) *PNAS* 88:7978–7982, the contents of all of which are incorporated by reference herein).

In one embodiment, the anti-53010 antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Method of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856–859; Green, L. L. et al. 1994 *Nature Genet.* 7:13–21; Morrison, S. L. et al. 1994 *Proc. Natl. Acad. Sci.*

USA 81:6851–6855; Bruggeman et al. 1993 *Year Immunol* 7:33-40; Tuaillon et al. 1993 *PNAS* 90:3720–3724; Bruggeman et al. 1991 Eur J Immunol 21:1323–1326).

An anti-53010 antibody can be one in which the variable region, or a portion thereof, e.g., the CDR's, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al. (1988 *Science* 240:1041–1043); Liu et al. (1987) *PNAS* 84:3439–3443; Liu et al., 1987, *J Immunol.* 139:3521–3526; Sun et al. (1987) *PNAS* 84:214–218; Nishimura et al., 1987, *Canc. Res.* 47:999–1005; Wood et al. (1985) *Nature* 314:446–449; and Shaw et al., 1988, *J. Natl Cancer Inst.* 80:1553–1559).

A humanized or CDR-grafted antibody will have at least one or two but generally all three recipient CDR's (of heavy and or light immuoglobulin chains) replaced with a donor CDR. The antibody may be replaced with at least a portion of a non-human CDR or only some of the CDR's may be replaced with non-human CDR's. It is only necessary to replace the number of CDR's required for binding of the humanized antibody to a 53010 or a fragment thereof. Preferably, the donor will be a rodent antibody, e.g., a rat or mouse antibody, and the recipient will be a human framework or a human consensus framework. Typically, the immunoglobulin providing the CDR's is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto. As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art. Humanized antibodies can be generated by replacing sequences of the Fv variable region which are not directly involved in antigen binding with equivalent sequences from human Fv variable regions. General methods for generating humanized antibodies are provided by Morrison, S. L., 1985, *Science* 229:1202–1207, by Oi et al., 1986, *BioTechniques* 4:214, and by Queen et al. U.S. Pat. No. 5,585,089, U.S. Pat. No. 5,693,761 and U.S. Pat. No. 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a 53010 polypeptide or fragment thereof. The recombinant DNA encoding the humanized antibody, or fragment thereof, can then be cloned into an appropriate expression vector.

Humanized or CDR-grafted antibodies can be produced by CDR-grafting or CDR substitution, wherein one, two, or all CDR's of an immunoglobulin chain can be replaced. See e.g., U.S. Pat. No. 5,225,539; Jones et al. 1986 *Nature* 321:552–525; Verhoeyan et al. 1988 *Science* 239:1534; Beidler et al. 1988 *J. Immunol.* 141:4053–4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Preferred humanized antibodies have amino acid substitutions in the framework region, such as to improve binding to the antigen. For example, a humanized antibody will have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12–16 of U.S. Pat. No. 5,585,089, the e.g., columns 12–16 of U.S. Pat. No. 5,585, 089, the contents of which are hereby incorporated by reference. Other techniques for humanizing antibodies are described in Padlan et al. EP 519596 A1, published on Dec. 23, 1992.

In preferred embodiments an antibody can be made by immunizing with purified 53010 antigen, or a fragment thereof, e.g., a fragment described herein, tissue, e.g., crude tissue preparations, whole cells, preferably living cells, lysed cells, or cell fractions.

A full-length 53010 protein or, antigenic peptide fragment of 53010 can be used as an immunogen or can be used to identify anti-53010 antibodies made with other immunogens, e.g., cells, membrane preparations, and the like. The antigenic peptide of 53010 should include at least 8 amino acid residues of the amino acid sequence shown in SEQ ID NO:2 and encompasses an epitope of 53010. Preferably, the antigenic peptide includes at least 10 amino acid residues, more preferably at least 15 amino acid residues, even more preferably at least 20 amino acid residues, and most preferably at least 30 amino acid residues.

Fragments of 53010 which include residues from about amino acid 51 to 80, from about 140 to 152, from about 232 to 248, and from about 410 to 435 of SEQ ID NO:2 can be used to make, e.g., used as immunogens or used to characterize the specificity of an antibody, antibodies against hydrophilic regions of the 53010 protein. Similarly, fragments of 53010 which include residues all or part of a hydrophilic sequence from about amino acid 190 to 205, from about 265 to 281, and from about 440 to 458 of SEQ ID NO:2 can be used to make an antibody against a hydrophobic region of the 53010 protein; a fragment of 53010 which include residues about 44 to 545, 219 to 234, or 125 to 135 can be used to make an antibody against the carboxylesterase region of the 53010 protein.

Antibodies reactive with, or specific for, any of these regions, or other regions or domains described herein are provided.

Antibodies which bind only native 53010 protein, only denatured or otherwise non-native 53010 protein, or which bind both, are with in the invention. Antibodies with linear or conformational epitopes are within the invention. Conformational epitopes can sometimes be identified by identifying antibodies which bind to native but not denatured 53010 protein.

Preferred epitopes encompassed by the antigenic peptide are regions of 53010 are located on the surface of the protein, e.g., hydrophilic regions, as well as regions with high antigenicity. For example, an Emini surface probability analysis of the human 53010 protein sequence can be used to indicate the regions that have a particularly high probability of being localized to the surface of the 53010 protein and are thus likely to constitute surface residues useful for targeting antibody production.

In preferred embodiments antibodies can bind one or more of purified antigen, tissue, e.g., tissue sections, whole cells, preferably living cells, lysed cells, or cell fractions.

The anti-53010 antibody can be a single chain antibody. A single-chain antibody (scFV) may be engineered (see, for example, Colcher, D. et al. (1999) *Ann N Y Acad Sci* 880:263–80; and Reiter, Y. (1996) *Clin Cancer Res* 2:245–52). The single chain antibody can be dimerized or multimerized to generate multivalent antibodies having specificities for different epitopes of the same target 53010 protein.

In a preferred embodiment the antibody has effector function and/or can fix complement. In other embodiments the antibody does not recruit effector cells; or fix complement.

In a preferred embodiment, the antibody has reduced or no ability to bind an Fc receptor. For example, it is a isotype or subtype, fragment or other mutant, which does not support binding to an Fc receptor, e.g., it has a mutagenized or deleted Fc receptor binding region.

In a preferred embodiment, an anti-53010 antibody alters (e.g., increases or decreases) the carboxylesterase activity of a 53010 polypeptide. For example, the antibody can bind at or in proximity to the active site, e.g., to an epitope that includes a residue located from about 125–135 of SEQ ID NO:2 or 219–234 of SEQ ID NO:2.

The antibody can be coupled to a toxin, e.g., a polypeptide toxin, e.g., ricin or diphtheria toxin or active fragment hereof, or a radioactive nucleus, or imaging agent, e.g. a radioactive, enzymatic, or other, e.g., imaging agent, e.g., a NMR contrast agent. Labels which produce detectable radioactive emissions or fluorescence are preferred.

An anti-53010 antibody (e.g., monoclonal antibody) can be used to isolate 53010 by standard techniques, such as affinity chromatography or immunoprecipitation. Moreover, an anti-53010 antibody can be used to detect 53010 protein (e.g., in a cellular lysate or cell supernatant) in order to evaluate the abundance and pattern of expression of the protein. Anti-53010 antibodies can be used diagnostically to monitor protein levels in tissue as part of a clinical testing procedure, e.g., to determine the efficacy of a given treatment regimen. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

The invention also includes a nucleic acid which encodes an anti-53010 antibody, e.g., an anti-53010 antibody described herein. Also included are vectors which include the nucleic acid and cells transformed with the nucleic acid, particularly cells which are useful for producing an antibody, e.g., mammalian cells, e.g. CHO or lymphatic cells.

The invention also includes cell lines, e.g., hybridomas, which make an anti-53010 antibody, e.g., an antibody described herein, and method of using said cells to make a 53010 antibody.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 53010 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 53010 proteins, mutant forms of 53010 proteins, fusion proteins, and the like).

The recombinant expression vectors of the invention can be designed for expression of 53010 proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 53010 activity assays, (e.g., direct assays or competitive assays described in detail below), or to generate antibodies specific for 53010 proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six weeks).

To maximize recombinant protein expression in *E. coli* is to express the protein in a host bacteria with an impaired capacity to proteolytically cleave the recombinant protein (Gottesman, S., (1990) *Gene Expression Technology: Methods in Enzymology* 185, Academic Press, San Diego, Calif. 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

The 53010 expression vector can be a yeast expression vector, a vector for expression in insect cells, e.g., a baculovirus expression vector or a vector suitable for expression in mammalian cells.

When used in mammalian cells, the expression vector's control functions can be provided by viral regulatory elements. For example, commonly used promoters are derived from polyoma, Adenovirus 2, cytomegalovirus and Simian Virus 40.

In another embodiment, the promoter is an inducible promoter, e.g., a promoter regulated by a steroid hormone, by a polypeptide hormone (e.g., by means of a signal transduction pathway), or by a heterologous polypeptide (e.g., the tetracycline-inducible systems, "Tet-On" and "Tet-Off"; see, e.g., Clontech Inc., Calif., Gossen and Bujard (1992) *Proc. Natl. Acad. Sci. USA* 89:5547, and Paillard (1989) *Human Gene Therapy* 9:983).

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus.

Another aspect the invention provides a host cell which includes a nucleic acid molecule described herein, e.g., a 53010 nucleic acid molecule within a recombinant expression vector or a 53010 nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 53010 protein can be expressed in bacterial cells (such as *E. coli*), insect cells, yeast or mammalian cells (such as Chinese hamster ovary cells (CHO) or COS cells (African green monkey kidney cells CV-1 origin SV40 cells; Gluzman (1981) *Cell* 23:175–182)). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a 53010 protein. Accordingly, the invention further provides methods for producing a 53010 protein using the host cells of the invention. In one embodiment, the method includes culturing the host cell of the invention (into which a recombinant expression vector encoding a 53010 protein has been introduced) in a suitable medium such that a 53010 protein is produced. In another embodiment, the method further includes isolating a 53010 protein from the medium or the host cell.

In another aspect, the invention features, a cell or purified preparation of cells which include a 53010 transgene, or which otherwise misexpress 53010. The cell preparation can consist of human or non-human cells, e.g., rodent cells, e.g., mouse or rat cells, rabbit cells, or pig cells. In preferred embodiments, the cell or cells include a 53010 transgene, e.g., a heterologous form of a 53010, e.g., a gene derived from humans (in the case of a non-human cell). The 53010 transgene can be misexpressed, e.g., overexpressed or underexpressed. In other preferred embodiments, the cell or cells include a gene that mis-expresses an endogenous 53010, e.g., a gene the expression of which is disrupted, e.g., a knockout. Such cells can serve as a model for studying disorders that are related to mutated or mis-expressed 53010 alleles or for use in drug screening.

In another aspect, the invention features, a human cell, e.g., a hematopoietic stem cell, transformed with nucleic acid which encodes a subject 53010 polypeptide.

Also provided are cells, preferably human cells, e.g., human hematopoietic or fibroblast cells, in which an endogenous 53010 is under the control of a regulatory sequence that does not normally control the expression of the endogenous 53010 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 53010 gene. For example, an endogenous 53010 gene which is "transcriptionally silent," e.g., not normally expressed, or expressed only at very low levels, may be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published in May 16, 1991.

In a preferred embodiment, recombinant cells described herein can be used for replacement therapy in a subject. For example, a nucleic acid encoding a 53010 polypeptide operably linked to an inducible promoter (e.g., a steroid hormone receptor-regulated promoter) is introduced into a human or nonhuman, e.g., mammalian, e.g., porcine recombinant cell. The cell is cultivated and encapsulated in a biocompatible material, such as poly-lysine alginate, and subsequently implanted into the subject. See, e.g., Lanza (1996) *Nat. Biotechnol* 14:1107; Joki et al. (2001) *Nat. Biotechnol.* 19:35; and U.S. Pat. No. 5,876,742. Production of 53010 polypeptide can be regulated in the subject by administering an agent (e.g., a steroid hormone) to the subject. In another preferred embodiment, the implanted recombinant cells express and secrete an antibody specific for a 53010 polypeptide. The antibody can be any antibody or any antibody derivative described herein.

Transgenic Animals

The invention provides non-human transgenic animals. Such animals are useful for studying the function and/or activity of a 53010 protein and for identifying and/or evaluating modulators of 53010 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 53010 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 53010 protein to particular cells. A transgenic founder animal can be identified based upon the presence of a 53010 transgene in its genome and/or expression of 53010 mRNA in tissues or cells of the animals. A transgenic founder animal can then be used to breed additional animals carrying the transgene. Moreover, transgenic animals carrying a transgene encoding a 53010 protein can further be bred to other transgenic animals carrying other transgenes.

53010 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed, e.g., below.

Uses

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). In addition, the 53010 polypeptides of the invention are useful in vitro for the chemical synthesis and/or modification of chemical compounds (e.g., for the stereospecific synthesis and hydrolysis of esters).

The isolated nucleic acid molecules of the invention can be used, for example, to express a 53010 protein (e.g., via a recombinant expression vector in a host cell in gene therapy applications), to detect a 53010 mRNA (e.g., in a biological sample) or a genetic alteration in a 53010 gene, and to modulate 53010 activity, as described further below. The 53010 proteins can be used to treat disorders characterized by insufficient or excessive production of a 53010 substrate or production of 53010 inhibitors. In addition, the 53010 proteins can be used to screen for naturally occurring 53010 substrates, to screen for drugs or compounds which modulate 53010 activity, as well as to treat disorders characterized by insufficient or excessive production of 53010 protein or production of 53010 protein forms which have decreased, aberrant or unwanted activity compared to 53010 wild type protein (e.g., pain or pain-related disorders). Moreover, the anti-53010 antibodies of the invention can be used to detect and isolate 53010 proteins, regulate the bioavailability of 53010 proteins, and modulate 53010 activity.

A method of evaluating a compound for the ability to interact with, e.g., bind, a subject 53010 polypeptide is provided. The method includes: contacting the compound with the subject 53010 polypeptide; and evaluating ability of the compound to interact with, e.g., to bind or form a complex with the subject 53010 polypeptide. This method can be performed in vitro, e.g., in a cell free system, or in vivo, e.g., in a two-hybrid interaction trap assay. This method can be used to identify naturally occurring molecules that interact with subject 53010 polypeptide. It can also be used to find natural or synthetic inhibitors of subject 53010 polypeptide. Screening methods are discussed in more detail below.

Screening Assays

The invention provides methods (also referred to herein as "screening assays") for identifying modulators, i.e., candidate or test compounds or agents (e.g., proteins, peptides, peptidomimetics, peptoids, small molecules or other drugs) which bind to 53010 proteins, have a stimulatory or inhibitory effect on, for example, 53010 expression or 53010 activity, or have a stimulatory or inhibitory effect on, for example, the expression or activity of a 53010 substrate. Compounds thus identified can be used to modulate the activity of target gene products (e.g., 53010 genes) in a therapeutic protocol, to elaborate the biological function of the target gene product, or to identify compounds that disrupt normal target gene interactions.

In one embodiment, the invention provides assays for screening candidate or test compounds which are substrates of a 53010 protein or polypeptide or a biologically active portion thereof. In another embodiment, the invention provides assays for screening candidate or test compounds that bind to or modulate an activity of a 53010 protein or polypeptide or a biologically active portion thereof.

A carboxylesterase activity of a 53010 polypeptide can be detected by an in vitro hydrolase activity assay well known in the art and can be found, for example, in Newcomb et al. (1997) *Proc. Natl Acad. Sci. USA* 94:7464–7468, Newcomb et al. (1996) *Insect Biochem. Mol. Biol.* 27:15–25, and Campbell et al. (1997) *Biochem. Genet.* 53:17–40. These assays include, but are not limited to, the disappearance of a substrate, or appearance of a product, e.g., by spectrophotometric measurement of artificial ester substrates, such as naphthyl acetate (NA), p-nitrophenyl acetate (p-NPA), and methylthiobutyrate (MtB), or by a radiometric measurement of labelled substrates, such as $^{14}C$-labelled esters.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) *J. Med. Chem.* 37:2678–85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994)*Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner, U.S. Pat. No. 5,223,409), spores (Ladner U.S. Pat. No. 5,223,409), plasmids (Cull et al. (1992) *Proc Natl Acad Sci USA* 89:1865–1869) or on phage (Scott and Smith (1990) *Science* 249:386–390; Devlin (1990) *Science* 249:404–406; Cwirla et al. (1990) *Proc. Natl. Acad. Sci.* 87:6378–6382; Felici (1991)*J. Mol. Biol.* 222:301–310;Ladner supra.).

In one embodiment, an assay is a cell-based assay in which a cell which expresses a 53010 protein or biologically active portion thereof is contacted with a test compound, and the ability of the test compound to modulate 53010 activity is determined. Determining the ability of the test compound to modulate 53010 activity can be accomplished by monitoring, for example, hydrolysis of carboxyl group. The cell, for example, can be of mammalian origin, e.g., human.

The ability of the test compound to modulate 53010 binding to a compound, e.g., a 53010 substrate, or to bind to 53010 can also be evaluated. This can be accomplished, for example, by coupling the compound, e.g., the substrate, with a radioisotope or enzymatic label such that binding of the compound, e.g., the substrate, to 53010 can be determined by detecting the labeled compound, e.g., substrate, in a complex. Alternatively, 53010 could be coupled with a radioisotope or enzymatic label to monitor the ability of a test compound to modulate 53010 binding to a 53010 substrate in a complex. For example, compounds (e.g., 53010 substrates) can be labeled with 125I, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 53010 substrate) to interact with 53010 with or without the labeling of any of the interactants can be evaluated. For example, a microphysiometer can be used to detect the interaction of a compound with 53010 without the labeling of either the compound or the 53010. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 53010.

In yet another embodiment, a cell-free assay is provided in which a 53010 protein or biologically active portion thereof is contacted with a test compound and the ability of the test compound to bind to the 53010 protein or biologically active portion thereof is evaluated. Preferred biologically active portions of the 53010 proteins to be used in assays of the present invention include fragments which participate in interactions with non-53010 molecules, e.g., fragments with high surface probability scores. Soluble and/or membrane-bound forms of isolated proteins (e.g., 53010 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 53010 protein to bind to a target molecule can be accomplished using real-time Biomolecular Interaction Analysis (BIA) (see, e.g., Sjolander, S. and Urbaniczky, C. (1991) Anal. Chem. 63:2338–2345 and Szabo et al. (1995) Curr. Opin. Struct. Biol. 5:699–705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either 53010, an anti-53010 antibody or its target molecule to facilitate separation of complexed from uncomplexed forms of one or both of the proteins, as well as to accommodate automation of the assay. Binding of a test compound to a 53010 protein, or interaction of a 53010 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/53010 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or 53010 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 53010 binding or activity determined using standard techniques.

Other techniques for immobilizing either a 53010 protein or a target molecule on matrices include using conjugation of biotin and streptavidin. Biotinylated 53010 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 53010 protein or target molecules but which do not interfere with binding of the 53010 protein to its target molecule. Such antibodies can be derivatized to the wells of the plate, and unbound target or 53010 protein trapped in the wells by antibody conjugation. Methods for detecting such complexes, in addition to those described above for the GST-immobilized complexes, include immunodetection of complexes using antibodies reactive with the 53010 protein or target molecule, as well as enzyme-linked assays which rely on detecting an enzymatic activity associated with the 53010 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., (1993) Trends Biochem Sci 18:284–7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al., eds. (1999) Current Protocols in Molecular Biology, J. Wiley: New York). Such resins and chromatographic techniques are known to one skilled in the art (see, e.g., Heegaard, N. H., (1998) J Mol Recognit 11:141–8; Hage, D. S., and Tweed, S. A. (1997) J Chromatogr B Biomed Sci Appl. 699:499–525). Further, fluorescence energy transfer may also be conveniently utilized, as described herein, to detect binding without further purification of the complex from solution.

In a preferred embodiment, the assay includes contacting the 53010 protein or biologically active portion thereof with a known compound which binds 53010 to form an assay mixture, contacting the assay mixture with a test compound, and determining the ability of the test compound to interact with a 53010 protein, wherein determining the ability of the test compound to interact with a 53010 protein includes determining the ability of the test compound to preferentially bind to 53010 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 53010 genes herein identified. In an alternative embodiment, the invention provides methods for determining the ability of the test compound to modulate the activity of a 53010 protein through modulation of the activity of a downstream effector of a 53010 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface, e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 53010 proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with 53010 ("53010-binding proteins" or "53010-bp") and are involved in 53010 activity. Such 53010-bps can be activators or inhibitors of signals by the 53010 proteins or 53010 targets as, for example, downstream elements of a 53010-mediated signaling pathway.

The two-hybrid system is based on the modular nature of most transcription factors, which consist of separable DNA-binding and activation domains. Briefly, the assay utilizes two different DNA constructs. In one construct, the gene that codes for a 53010 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: 53010 protein can be the fused to the activator domain.) If the "bait" and the "prey" proteins are able to interact, in vivo, forming a 53010-dependent complex, the DNA-binding and activation domains of the transcription factor are brought into close proximity. This proximity allows transcription of a reporter gene (e.g., lacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 53010 protein.

In another embodiment, modulators of 53010 expression are identified. For example, a cell or cell free mixture is contacted with a candidate compound and the expression of 53010 mRNA or protein evaluated relative to the level of expression of 53010 mRNA or protein in the absence of the candidate compound. When expression of 53010 mRNA or protein is greater in the presence of the candidate compound than in its absence, the candidate compound is identified as a stimulator of 53010 mRNA or protein expression. Alternatively, when expression of 53010 mRNA or protein is less (statistically significantly less) in the presence of the candidate compound than in its absence, the candidate compound is identified as an inhibitor of 53010 mRNA or protein expression. The level of 53010 mRNA or protein expression can be determined by methods described herein for detecting 53010 mRNA or protein.

In another aspect, the invention pertains to a combination of two or more of the assays described herein. For example, a modulating agent can be identified using a cell-based or a cell free assay, and the ability of the agent to modulate the activity of a 53010 protein can be confirmed in vivo, e.g., in an animal such as an animal model for lacking ability of hydrolysis of carboxylic esters.

This invention further pertains to novel agents identified by the above-described screening assays. Accordingly, it is within the scope of this invention to further use an agent identified as described herein (e.g., a 53010 modulating agent, an antisense 53010 nucleic acid molecule, a 53010-specific antibody, or a 53010-binding partner) in an appropriate animal model to determine the efficacy, toxicity, side effects, or mechanism of action, of treatment with such an agent. Furthermore, novel agents identified by the above-described screening assays can be used for treatments as described herein.

Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 53010 with a disease; (ii) identify an individual from a minute biological sample (tissue typing); and (iii) aid in forensic identification of a biological sample. These applications are described in the subsections below.

Chromosome Mapping

The 53010 nucleotide sequences or portions thereof can be used to map the location of the 53010 genes on a chromosome. This process is called chromosome mapping. Chromosome mapping is useful in correlating the 53010 sequences with genes associated with disease.

Briefly, 53010 genes can be mapped to chromosomes by preparing PCR primers (preferably 15–25 bp in length) from the 53010 nucleotide sequences. These primers can then be used for PCR screening of somatic cell hybrids containing individual human chromosomes. Only those hybrids containing the human gene corresponding to the 53010 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio P. et al. (1983) *Science* 220:919–924).

Other mapping strategies e.g., in situ hybridization (described in Fan, Y. et al. (1990) *Proc. Natl. Acad. Sci. USA*, 87:6223–27), pre-screening with labeled flow-sorted chromosomes, and pre-selection by hybridization to chromosome specific cDNA libraries can be used to map 53010 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques ((1988) Pergamon Press, New York).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783–787.

Moreover, differences in the DNA sequences between individuals affected and unaffected with a disease associated with the 53010 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing 53010 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 53010 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500–2,000.

If a panel of reagents from 53010 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 53010 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 (e.g., fragments derived from the noncoding regions of SEQ ID NO:1 having a length of at least 20 bases, preferably at least 30 bases) are particularly appropriate for this use.

The 53010 nucleotide sequences described herein can further be used to provide polynucleotide reagents, e.g., labeled or labelable probes which can be used in, for example, an in situ hybridization technique, to identify a specific tissue. This can be very useful in cases where a forensic pathologist is presented with a tissue of unknown origin. Panels of such 53010 probes can be used to identify tissue by species and/or by organ type.

In a similar fashion, these reagents, e.g., 53010 primers or probes can be used to screen tissue culture for contamination (i.e. screen for the presence of a mixture of different types of cells in a culture).

Predictive Medicine

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes 53010.

Such disorders include, e.g., a disorder associated with the misexpression of 53010 gene; a disorder a disorder involving aberrant or deficient hydrolysis of carboxylic esters; pain or pain-related disorders; and a disorder of the blood coagulation system.

The method includes one or more of the following:

detecting, in a tissue of the subject, the presence or absence of a mutation which affects the expression of the 53010 gene, or detecting the presence or absence of a mutation in a region which controls the expression of the gene, e.g., a mutation in the 5' control region;

detecting, in a tissue of the subject, the presence or absence of a mutation which alters the structure of the 53010 gene;

detecting, in a tissue of the subject, the misexpression of the 53010 gene, at the mRNA level, e.g., detecting a non-wild type level of a mRNA;

detecting, in a tissue of the subject, the misexpression of the gene, at the protein level, e.g., detecting a non-wild type level of a 53010 polypeptide.

In preferred embodiments the method includes: ascertaining the existence of at least one of: a deletion of one or more nucleotides from the 53010 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:1, or naturally occurring mutants thereof or 5' or 3' flanking sequences naturally associated with the 53010 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 53010 gene; the presence of a non-wild type splicing pattern of a messenger RNA transcript of the gene; or a non-wild type level of 53010.

Methods of the invention can be used prenatally or to determine if a subject's offspring will be at risk for a disorder.

In preferred embodiments the method includes determining the structure of a 53010 gene, an abnormal structure being indicative of risk for the disorder.

In preferred embodiments the method includes contacting a sample from the subject with an antibody to the 53010 protein or a nucleic acid, which hybridizes specifically with the gene. These and other embodiments are discussed below.

Diagnostic and Prognostic Assays

Diagnostic and prognostic assays of the invention include method for assessing the expression level of 53010 molecules and for identifying variations and mutations in the sequence of 53010 molecules.

Expression Monitoring and Profiling

The presence, level, or absence of 53010 protein or nucleic acid in a biological sample can be evaluated by obtaining a biological sample from a test subject and contacting the biological sample with a compound or an agent capable of detecting 53010 protein or nucleic acid (e.g., mRNA, genomic DNA) that encodes 53010 protein such that the presence of 53010 protein or nucleic acid is detected in the biological sample. The term "biological sample" includes tissues, cells and biological fluids isolated from a subject, as well as tissues, cells and fluids present within a subject. A preferred biological sample is serum. The level of expression of the 53010 gene can be measured in a number of ways, including, but not limited to: measuring the mRNA encoded by the 53010 genes; measuring the amount of protein encoded by the 53010 genes; or measuring the activity of the protein encoded by the 53010 genes.

The level of mRNA corresponding to the 53010 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 53010 nucleic acid, such as the nucleic acid of SEQ ID NO: 1, or a portion thereof, such as an oligonucleotide of at least 7, 15, 30, 50, 100, 250 or 500 nucleotides in length and sufficient to specifically hybridize under stringent conditions to 53010 mRNA or genomic DNA. The probe can be disposed on an address of an array, e.g., an array described below. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the 53010 genes.

The level of mRNA in a sample that is encoded by one of 53010 can be evaluated with nucleic acid amplification, e.g., by rtPCR (Mullis (1987) U.S. Pat. No. 4,683,202), ligase chain reaction (Barany (1991) *Proc. Natl. Acad. Sci. USA* 88:189–193), self sustained sequence replication (Guatelli et al., (1990) *Proc. Natl. Acad. Sci. USA* 87:1874–1878), transcriptional amplification system (Kwoh et al., (1989) *Proc. Natl. Acad. Sci. USA* 86:1173–1177), Q-Beta Replicase (Lizardi et al., (1988) *Bio/Technology* 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 53010 gene being analyzed.

In another embodiment, the methods further contacting a control sample with a compound or agent capable of detecting 53010 mRNA, or genomic DNA, and comparing the presence of 53010 mRNA or genomic DNA in the control sample with the presence of 53010 mRNA or genomic DNA in the test sample. In still another embodiment, serial analysis of gene expression, as described in U.S. Pat. No. 5,695,937, is used to detect 53010 transcript levels.

A variety of methods can be used to determine the level of protein encoded by 53010. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 53010 protein in a biological sample in vitro as well as in vivo. In vitro techniques for detection of 53010 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 53010 protein include introducing into a subject a labeled anti-53010 antibody. For example, the antibody can be labeled with a radioactive marker whose presence and location in a subject can be detected by standard imaging techniques. In another embodiment, the sample is labeled, e.g., biotinylated and then contacted to the antibody, e.g., an anti-53010 antibody positioned on an antibody array (as described below). The sample can be detected, e.g., with avidin coupled to a fluorescent label.

In another embodiment, the methods further include contacting the control sample with a compound or agent capable of detecting 53010 protein, and comparing the presence of 53010 protein in the control sample with the presence of 53010 protein in the test sample.

The invention also includes kits for detecting the presence of 53010 in a biological sample. For example, the kit can include a compound or agent capable of detecting 53010 protein or mRNA in a biological sample; and a standard. The compound or agent can be packaged in a suitable container. The kit can further comprise instructions for using the kit to detect 53010 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 53010 expression or activity. As used herein, the term "unwanted" includes an unwanted phenomenon involved in a biological response such as pain or deregulated cell proliferation.

In one embodiment, a disease or disorder associated with aberrant or unwanted 53010 expression or activity is identified. A test sample is obtained from a subject and 53010 protein or nucleic acid (e.g., mRNA or genomic DNA) is evaluated, wherein the level, e.g., the presence or absence, of 53010 protein or nucleic acid is diagnostic for a subject having or at risk of developing a disease or disorder associated with aberrant or unwanted 53010 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 53010 expression or activity. For example, such methods can be used to determine whether a subject can be effectively treated with an agent for pain or a pain-related disorder.

In another aspect, the invention features a computer medium having a plurality of digitally encoded data records. Each data record includes a value representing the level of expression of 53010 in a sample, and a descriptor of the sample. The descriptor of the sample can be an identifier of the sample, a subject from which the sample was derived (e.g., a patient), a diagnosis, or a treatment (e.g., a preferred treatment). In a preferred embodiment, the data record further includes values representing the level of expression of genes other than 53010 (e.g., other genes associated with a 53010-disorder, or other genes on an array). The data record can be structured as a table, e.g., a table that is part of a database such as a relational database (e.g., a SQL database of the Oracle or Sybase database environments).

Also featured is a method of evaluating a sample. The method includes providing a sample, e.g., from the subject, and determining a gene expression profile of the sample, wherein the profile includes a value representing the level of 53010 expression. The method can further include comparing the value or the profile (i.e., multiple values) to a reference value or reference profile. The gene expression profile of the sample can be obtained by any of the methods described herein (e.g., by providing a nucleic acid from the sample and contacting the nucleic acid to an array). The method can be used to diagnose a pain-related disorder in a subject wherein an unwanted 53010 expression is an indication that the subject has or is disposed to having a pain-related disorder. The method can be used to monitor a treatment for a pain-related disorder in a subject. For example, the gene expression profile can be determined for a sample from a subject undergoing treatment. The profile can be compared to a reference profile or to a profile obtained from the subject prior to treatment or prior to onset of the disorder (see, e.g., Golub et al. (1999) *Science* 286:531).

In yet another aspect, the invention features a method of evaluating a test compound (see also, "Screening Assays", above). The method includes providing a cell and a test compound; contacting the test compound to the cell; obtaining a subject expression profile for the contacted cell; and comparing the subject expression profile to one or more reference profiles. The profiles include a value representing the level of 53010 expression. In a preferred embodiment, the subject expression profile is compared to a target profile, e.g., a profile for a normal cell or for desired condition of a cell. The test compound is evaluated favorably if the subject expression profile is more similar to the target profile than an expression profile obtained from an uncontacted cell.

In another aspect, the invention features, a method of evaluating a subject. The method includes: a) obtaining a sample from a subject, e.g., from a caregiver, e.g., a caregiver who obtains the sample from the subject; b) determining a subject expression profile for the sample. Optionally, the method further includes either or both of steps: c) comparing the subject expression profile to one or more reference expression profiles; and d) selecting the reference profile most similar to the subject reference profile. The subject expression profile and the reference profiles include a value representing the level of 53010 expression. A variety of routine statistical measures can be used to compare two reference profiles. One possible metric is the length of the distance vector that is the difference between the two profiles. Each of the subject and reference profile is represented as a multi-dimensional vector, wherein each dimension is a value in the profile.

The method can further include transmitting a result to a caregiver. The result can be the subject expression profile, a result of a comparison of the subject expression profile with another profile, a most similar reference profile, or a descriptor of any of the aforementioned. The result can be transmitted across a computer network, e.g., the result can be in the form of a computer transmission, e.g., a computer data signal embedded in a carrier wave.

Also featured is a computer medium having executable code for effecting the following steps: receive a subject expression profile; access a database of reference expression profiles; and either i) select a matching reference profile most similar to the subject expression profile or ii) determine at least one comparison score for the similarity of the subject expression profile to at least one reference profile. The subject expression profile, and the reference expression profiles each include a value representing the level of 53010 expression.

Arrays and Uses Thereof

In another aspect, the invention features an array that includes a substrate having a plurality of addresses. At least one address of the plurality includes a capture probe that binds specifically to a 53010 molecule (e.g., a 53010 nucleic acid or a 53010 polypeptide). The array can have a density of at least than 10, 50, 100, 200, 500, 1,000, 2,000, or 10,000 or more addresses/cm², and ranges between. In a preferred embodiment, the plurality of addresses includes at least 10, 100, 500, 1,000, 5,000, 10,000, 50,000 addresses. In a preferred embodiment, the plurality of addresses includes equal to or less than 10, 100, 500, 1,000, 5,000, 10,000, or 50,000 addresses. The substrate can be a two-dimensional substrate such as a glass slide, a wafer (e.g., silica or plastic), a mass spectroscopy plate, or a three-dimensional substrate such as a gel pad. Addresses in addition to address of the plurality can be disposed on the array.

In a preferred embodiment, at least one address of the plurality includes a nucleic acid capture probe that hybridizes specifically to a 53010 nucleic acid, e.g., the sense or anti-sense strand. In one preferred embodiment, a subset of addresses of the plurality of addresses has a nucleic acid capture probe for 53010. Each address of the subset can include a capture probe that hybridizes to a different region of a 53010 nucleic acid. In another preferred embodiment, addresses of the subset include a capture probe for a 53010 nucleic acid. Each address of the subset is unique, overlapping, and complementary to a different variant of 53010 (e.g., an allelic variant, or all possible hypothetical variants). The array can be used to sequence 53010 by hybridization (see, e.g., U.S. Pat. No. 5,695,940).

An array can be generated by various methods, e.g., by photolithographic methods (see, e.g., U.S. Pat. Nos. 5,143, 854; 5,510,270; and 5,527,681), mechanical methods (e.g., directed-flow methods as described in U.S. Pat. No. 5,384, 261), pin-based methods (e.g., as described in U.S. Pat. No. 5,288,514), and bead-based techniques (e.g., as described in PCT US/93/04145).

In another preferred embodiment, at least one address of the plurality includes a polypeptide capture probe that binds specifically to a 53010 polypeptide or fragment thereof. The polypeptide can be a naturally-occurring interaction partner of 53010 polypeptide. Preferably, the polypeptide is an antibody, e.g., an antibody described herein (see "Anti-53010 Antibodies," above), such as a monoclonal antibody or a single-chain antibody.

In another aspect, the invention features a method of analyzing the expression of 53010. The method includes providing an array as described above; contacting the array with a sample and detecting binding of a 53010-molecule (e.g., nucleic acid or polypeptide) to the array. In a preferred embodiment, the array is a nucleic acid array. Optionally the method further includes amplifying nucleic acid from the sample prior or during contact with the array.

In another embodiment, the array can be used to assay gene expression in a tissue to ascertain tissue specificity of genes in the array, particularly the expression of 53010. If a sufficient number of diverse samples is analyzed, clustering (e.g., hierarchical clustering, k-means clustering, Bayesian clustering and the like) can be used to identify other genes which are co-regulated with 53010. For example, the array can be used for the quantitation of the expression of multiple genes. Thus, not only tissue specificity, but also the level of expression of a battery of genes in the tissue is ascertained. Quantitative data can be used to group (e.g., cluster) genes on the basis of their tissue expression per se and level of expression in that tissue.

For example, array analysis of gene expression can be used to assess the effect of cell—cell interactions on 53010 expression. A first tissue can be perturbed and nucleic acid from a second tissue that interacts with the first tissue can be analyzed. In this context, the effect of one cell type on another cell type in response to a biological stimulus can be determined, e.g., to monitor the effect of cell—cell interaction at the level of gene expression.

In another embodiment, cells are contacted with a therapeutic agent. The expression profile of the cells is determined using the array, and the expression profile is compared to the profile of like cells not contacted with the agent. For example, the assay can be used to determine or analyze the molecular basis of an undesirable effect of the therapeutic agent. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor expression of one or more genes in the array with respect to time. For example, samples obtained from different time points can be probed with the array. Such analysis can identify and/or characterize the development of a 53010-associated disease or disorder; and processes, such as a cellular transformation associated with a 53010-associated disease or disorder. The method can also evaluate the treatment and/or progression of a 53010-associated disease or disorder The array is also useful for ascertaining differential expression patterns of one or more genes in normal and abnormal cells. This provides a battery of genes (e.g., including 53010) that could serve as a molecular target for diagnosis or therapeutic intervention.

In another aspect, the invention features an array having a plurality of addresses. Each address of the plurality includes a unique polypeptide. At least one address of the plurality has disposed thereon a 53010 polypeptide or fragment thereof. Methods of producing polypeptide arrays are described in the art, e.g., in De Wildt et al. (2000). *Nature Biotech.* 18, 989–994; Lueking et al. (1999). *Anal. Biochem.* 270, 103–111; Ge, H. (2000). *Nucleic Acids Res.* 28, e3, I–VII; MacBeath, G., and Schreiber, S. L. (2000). *Science* 289, 1760–1763; and WO 99/51773A1. In a preferred embodiment, each addresses of the plurality has disposed thereon a polypeptide at least 60, 70, 80, 85, 90, 95 or 99% identical to a 53010 polypeptide or fragment thereof. For example, multiple variants of a 53010 polypeptide (e.g., encoded by allelic variants, site-directed mutants, random mutants, or combinatorial mutants) can be disposed at individual addresses of the plurality. Addresses in addition to the address of the plurality can be disposed on the array.

The polypeptide array can be used to detect a 53010 binding compound, e.g., an antibody in a sample from a subject with specificity for a 53010 polypeptide or the presence of a 53010-binding protein or ligand.

The array is also useful for ascertaining the effect of the expression of a gene on the expression of other genes in the same cell or in different cells (e.g., ascertaining the effect of 53010 expression on the expression of other genes). This provides, for example, for a selection of alternate molecular targets for therapeutic intervention if the ultimate or downstream target cannot be regulated.

In another aspect, the invention features a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express 53010 or from a cell or subject in which a 53010 mediated response has been elicited, e.g., by contact of the cell with 53010 nucleic acid or protein, or administration to the cell or subject 53010 nucleic acid or protein; providing a two dimensional array having a plurality of addresses, each address of the plurality being positionally distinguishable from each other address of the plurality, and each address of the plurality having a unique capture probe, e.g., wherein the capture probes are from a cell or subject which does not express 53010 (or does not express as highly as in the case of the 53010 positive plurality of capture probes) or from a cell or subject which in which a 53010 mediated response has not been elicited (or has been elicited to a lesser extent than in the first sample); contacting the array with one or more inquiry probes (which is preferably other than a 53010 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features a method of analyzing a plurality of probes or a sample. The method is useful, e.g., for analyzing gene expression. The method includes: providing a two dimensional array having a plurality of addresses, each address of the plurality being positionally distinguishable from each other address of the plurality having a unique capture probe, contacting the array with a first sample from a cell or subject which express or mis-express 53010 or from a cell or subject in which a 53010-mediated response has been elicited, e.g., by contact of the cell with 53010 nucleic acid or protein, or administration to the cell or subject 53010 nucleic acid or protein; providing a two dimensional array having a plurality of addresses, each address of the plurality being positionally distinguishable from each other address of the plurality, and each address of the plurality having a unique capture probe, and contacting the array with a second sample from a cell or subject which does not express 53010 (or does not express as highly as in the case of the 53010 positive plurality of capture probes) or from a cell or subject which in which a 53010 mediated response has not been elicited (or has been elicited to a lesser extent than in the first sample); and comparing the binding of the first sample with the binding of the second sample. Binding, e.g., in the case of a nucleic acid, hybridization with a capture probe at an address of the plurality, is detected, e.g., by signal generated from a label attached to the nucleic acid, polypeptide, or antibody. The same array can be used for both samples or different arrays can be used. If different arrays are used the plurality of addresses with capture probes should be present on both arrays.

In another aspect, the invention features a method of analyzing 53010, e.g., analyzing structure, function, or relatedness to other nucleic acid or amino acid sequences. The method includes: providing a 53010 nucleic acid or amino acid sequence; comparing the 53010 sequence with one or more preferably a plurality of sequences from a collection of sequences, e.g., a nucleic acid or protein sequence database; to thereby analyze 53010.

Detection of Variations or Mutations

The methods of the invention can also be used to detect genetic alterations in a 53010 gene, thereby determining if a subject with the altered gene is at risk for a disorder characterized by misregulation in 53010 protein activity or nucleic acid expression, such as pain or a pain-related disorder. In preferred embodiments, the methods include detecting, in a sample from the subject, the presence or absence of a genetic alteration characterized by at least one of an alteration affecting the integrity of a gene encoding a 53010-protein, or the mis-expression of the 53010 gene. For example, such genetic alterations can be detected by ascertaining the existence of at least one of 1) a deletion of one or more nucleotides from a 53010 gene; 2) an addition of one or more nucleotides to a 53010 gene; 3) a substitution of one or more nucleotides of a 53010 gene, 4) a chromosomal rearrangement of a 53010 gene; 5) an alteration in the level of a messenger RNA transcript of a 53010 gene, 6) aberrant modification of a 53010 gene, such as of the methylation pattern of the genomic DNA, 7) the presence of a non-wild type splicing pattern of a messenger RNA transcript of a 53010 gene, 8) a non-wild type level of a 53010-protein, 9) allelic loss of a 53010 gene, and 10) inappropriate post-translational modification of a 53010-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 53010-gene. This method can include the steps of collecting a sample of cells from a subject, isolating nucleic acid (e.g., genomic, mRNA or both) from the sample, contacting the nucleic acid sample with one or more primers which specifically hybridize to a 53010 gene under conditions such that hybridization and amplification of the 53010-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternatively, other amplification methods described herein or known in the art can be used.

In another embodiment, mutations in a 53010 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 53010 can be identified by hybridizing a sample and control nucleic acids, e.g., DNA or RNA, two-dimensional arrays, e.g., chip based arrays. Such arrays include a plurality of addresses, each of which is positionally distinguishable from the other. A different probe is located at each address of the plurality. A probe can be complementary to a region of a 53010 nucleic acid or a putative variant (e.g., allelic variant) thereof. A probe can have one or more mismatches to a region of a 53010 nucleic acid (e.g., a destabilizing mismatch). The arrays can have a high density of addresses, e.g., can contain hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in 53010 can be identified in two-dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 53010 gene and detect mutations by comparing the sequence of the sample 53010 with the corresponding wild-type (control) sequence. Automated sequencing procedures can be utilized when performing the diagnostic assays ((1995) *Biotechniques* 19:448), including sequencing by mass spectrometry.

Other methods for detecting mutations in the 53010 gene include methods in which protection from cleavage agents is used to detect mismatched bases in RNA/RNA or RNA/DNA heteroduplexes (Myers et al. (1985) *Science* 230:1242; Cotton et al. (1988) *Proc. Natl Acad Sci USA* 85:4397; Saleeba et al. (1992) *Methods Enzymol.* 217:286–295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 53010 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) Carcinogenesis 15:1657–1662; U.S. Pat. No. 5,459,039).

In other embodiments, alterations in electrophoretic mobility will be used to identify mutations in 53010 genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125–144; and Hayashi (1992) *Genet. Anal. Tech. Appl.* 9:73–79). Single-stranded DNA fragments of sample and control 53010 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl Acad. Sci USA* 86:6230). A further method of detecting point mutations is the chemical ligation of oligonucleotides as described in Xu et al. ((2001) *Nature Biotechnol.* 19:148). Adjacent oligonucleotides, one of which selectively anneals to the query site, are ligated together if the nucleotide at the query site of the sample nucleic acid is complementary to the query oligonucleotide; ligation can be monitored, e.g., by fluorescent dyes coupled to the oligonucleotides.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

In another aspect, the invention features a set of oligonucleotides. The set includes a plurality of oligonucleotides, each of which is at least partially complementary (e.g., at least 50%, 60%, 70%, 80%, 90%, 92%, 95%, 97%, 98%, or 99% complementary) to a 53010 nucleic acid.

In a preferred embodiment the set includes a first and a second oligonucleotide. The first and second oligonucleotide can hybridize to the same or to different locations of SEQ ID NO:1 or the complement of SEQ ID NO: 1. Different locations can be different but overlapping, or non-overlapping on the same strand. The first and second oligonucleotide can hybridize to sites on the same or on different strands.

The set can be useful, e.g., for identifying SNP's, or identifying specific alleles of 53010. In a preferred embodiment, each oligonucleotide of the set has a different nucleotide at an interrogation position. In one embodiment, the set includes two oligonucleotides, each complementary to a different allele at a locus, e.g., a biallelic or polymorphic locus.

In another embodiment, the set includes four oligonucleotides, each having a different nucleotide (e.g., adenine, guanine, cytosine, or thymidine) at the interrogation position. The interrogation position can be a SNP or the site of a mutation. In another preferred embodiment, the oligonucleotides of the plurality are identical in sequence to one another (except for differences in length). The oligonucleotides can be provided with differential labels, such that an oligonucleotide that hybridizes to one allele provides a signal that is distinguishable from an oligonucleotide that hybridizes to a second allele. In still another embodiment, at least one of the oligonucleotides of the set has a nucleotide change at a position in addition to a query position, e.g., a destabilizing mutation to decrease the Tm of the oligonucleotide. In another embodiment, at least one oligonucleotide of the set has a non-natural nucleotide, e.g., inosine. In a preferred embodiment, the oligonucleotides are attached to a solid support, e.g., to different addresses of an array or to different beads or nanoparticles.

In a preferred embodiment the set of oligo nucleotides can be used to specifically amplify, e.g., by PCR, or detect, a 53010 nucleic acid.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a 53010 gene.

Use of 53010 Molecules as Surrogate Markers

The 53010 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 53010 molecules of the invention may be detected, and may be correlated with one or more biological states in vivo. For example, the 53010 molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258–264; and James (1994) *AIDS Treatment News Archive* 209.

The 53010 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a 53010 marker) transcription or expression, the amplified marker may be in a quantity which is more readily detectable than the drug itself. Also, the marker may be more easily detected due to the nature of the marker itself; for example, using the methods described herein, anti-53010 antibodies may be employed in an immune-based detection system for a 53010 protein marker, or 53010-specific radiolabeled probes may be used to detect a 53010 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229–238; Schentag (1999) *Am. J. Health-Syst. Pharm.* 56 Suppl. 3: S21–S24; and Nicolau (1999) *Am, J. Health-Syst. Pharm.* 56 Suppl. 3: S16–S20.

The 53010 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35:1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., 53010 protein or RNA) for specific tumor markers in a subject, a drug or course of treatment may be selected that is optimized for the treatment of the specific tumor likely to be present in the subject. Similarly, the presence or absence of a specific sequence mutation in 53010 DNA may correlate 53010 drug response. The use of pharmacogenomic markers therefore permits the application of the most appropriate treatment for each subject without having to administer the therapy.

Pharmaceutical Compositions

The nucleic acid and polypeptides, fragments thereof, as well as anti-53010 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies.

Accordingly, lower dosages and less frequent administration is often possible.

Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The present invention encompasses agents which modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e.,. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846,545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids). Radioactive ions include, but are not limited to iodine, yttrium and praseodymium.

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors. Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment

The present invention provides for both prophylactic and therapeutic methods of treating a subject at risk of (or susceptible to) a disorder or having a disorder associated with aberrant or unwanted 53010 expression or activity. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 53010 molecules of the present invention or 53010 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted 53010 expression or activity, by administering to the subject a 53010 or an agent which modulates 53010 expression or at least one 53010 activity. Subjects at risk for a disease which is caused or contributed to by aberrant or unwanted 53010 expression or activity can be identified by, for example, any or a combination of diagnostic or prognostic assays as described herein. Administration of a prophylactic agent can occur prior to the manifestation of symptoms characteristic of the 53010 aberrance, such that a disease or disorder is prevented or, alternatively, delayed in its progression. Depending on the type of 53010 aberrance, for example, a 53010, 53010 agonist or 53010 antagonist agent can be used for treating the subject. The appropriate agent can be determined based on screening assays described herein.

It is possible that some 53010 disorders can be caused, at least in part, by an abnormal level of gene product, or by the presence of a gene product exhibiting abnormal activity. As such, the reduction in the level and/or activity of such gene products would bring about the amelioration of disorder symptoms.

The 53010 molecules can act as novel diagnostic targets and therapeutic agents for controlling one or more of cellular proliferative and/or differentiative disorders, disorders associated with bone metabolism, immune disorders, cardiovascular disorders, liver disorders, viral diseases, blood clotting disorders, or hematopoietic disorders.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) *Crit Rev. in Oncol./Hemotol.* 11:267–97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Aberrant expression and/or activity of 53010 molecules may mediate disorders associated with bone metabolism. "Bone metabolism" refers to direct or indirect effects in the formation or degeneration of bone structures, e.g., bone formation, bone resorption, etc., which may ultimately affect the concentrations in serum of calcium and phosphate. This term also includes activities mediated by 53010 molecules effects in bone cells, e.g. osteoclasts and osteoblasts, that may in turn result in bone formation and degeneration. For example, 53010 molecules may support different activities of bone resorbing osteoclasts such as the stimulation of differentiation of monocytes and mononuclear phagocytes into osteoclasts. Accordingly, 53010 molecules that modulate the production of bone cells can influence bone formation and degeneration, and thus may be used to treat bone disorders. Examples of such disorders include, but are not limited to, osteoporosis, osteodystrophy, osteomalacia, rickets, osteitis fibrosa cystica, renal osteodystrophy, osteosclerosis, anti-convulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

The 53010 nucleic acid and protein of the invention can be used to treat and/or diagnose a variety of immune disorders. Examples of immune disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjogren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Examples of disorders involving the heart or "cardiovascular disorder" include, but are not limited to, a disease, disorder, or state involving the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. Examples of such disorders include hypertension, atherosclerosis, coronary artery spasm, congestive heart failure, coronary artery disease, valvular disease, arrhythmias, and cardiomyopathies.

Disorders which may be treated or diagnosed by methods described herein include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolism, for example, fibrosis resulting from a storage disorder such as Gaucher's disease (lipid abnormalities) or a glycogen storage disease, A1-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein may be useful for the early detection and treatment of liver injury associated with the administration of various chemicals or drugs, such as for example, methotrexate, isonizaid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

Additionally, 53010 molecules may play an important role in the etiology of certain viral diseases, including but not limited to Hepatitis B, Hepatitis C and Herpes Simplex Virus (HSV). Modulators of 53010 activity could be used to control viral diseases. The modulators can be used in the treatment and/or diagnosis of viral infected tissue or virus-associated tissue fibrosis, especially liver and liver fibrosis. Also, 53010 modulators can be used in the treatment and/or diagnosis of virus-associated carcinoma, especially hepatocellular cancer.

Examples of blood clotting disorders include vascular disorders caused by either partial or total occlusion of a blood vessel by a blood clot, such as stroke, deep vein thrombosis, peripheral arterial occlusion, pulmonary embolism, and myocardial thrombosis, as well as disorders involving defective-coagulation, e.g., hemophilia (e.g., Hemophilia A and Hemophilia B).

As discussed, successful treatment of 53010 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 53010 disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and Fab, F(ab')$_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by 53010 expression is through the use of aptamer molecules specific for 53010 protein. Aptamers are nucleic acid molecules having a tertiary structure which permits them to specifically bind to protein ligands (see, e.g., Osborne, et al. (1997) *Curr. Opin. Chem Biol.* 1: 5–9; and Patel, D. J. (1997) *Curr Opin Chem Biol* 1:32–46). Since nucleic acid molecules may in many cases be more conveniently introduced into target cells than therapeutic protein molecules may be, aptamers offer a method by which 53010 protein activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of 53010 disorders. For a description of antibodies, see the Antibody section above.

In circumstances wherein injection of an animal or a human subject with a 53010 protein or epitope for stimulating antibody production is harmful to the subject, it is possible to generate an immune response against 53010 through the use of anti-idiotypic antibodies (see, for example, Herlyn, D. (1999) *Ann Med* 31:66–78; and Bhattacharya-Chatterjee, M., and Foon, K. A. (1998) *Cancer Treat Res.* 94:51–68). If an anti-idiotypic antibody is introduced into a mammal or human subject, it should stimulate the production of anti-anti-idiotypic antibodies, which should be specific to the 53010 protein. Vaccines directed to a disease characterized by 53010 expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993) *Proc. Natl. Acad. Sci. USA* 90:7889–7893).

The identified compounds that inhibit target gene expression, synthesis and/or activity can be administered to a patient at therapeutically effective doses to prevent, treat or ameliorate 53010 disorders. A therapeutically effective dose refers to that amount of the compound sufficient to result in amelioration of symptoms of the disorders. Toxicity and therapeutic efficacy of such compounds can be determined by standard pharmaceutical procedures as described above.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography. Another example of determination of effective dose for an individual is the ability to directly assay levels of "free" and "bound" compound in the serum of the test subject. Such assays may utilize antibody mimics and/or "biosensors" that have been created through molecular imprinting techniques. The compound which is able to modulate 53010 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell, R. J. et al (1996) *Current Opinion in Biotechnology* 7:89–94 and in Shea, K. J. (1994) *Trends in Polymer Science* 2:166–173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis, G. et al (1993) *Nature* 361:645–647. Through the use of isotope-labeling, the "free" concentration of compound which modulates the expression or activity of 53010 can be readily monitored and used in calculations of $IC_{50}$. Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. An rudimentary example of such a "biosensor" is discussed in Kriz, D. et al (1995) *Analytical Chemistry* 67:2142–2144.

Another aspect of the invention pertains to methods of modulating 53010 expression or activity for therapeutic purposes. Accordingly, in an exemplary embodiment, the modulatory method of the invention involves contacting a cell with a 53010 or agent that modulates one or more of the activities of 53010 protein activity associated with the cell. An agent that modulates 53010 protein activity can be an agent as described herein, such as a nucleic acid or a protein, a naturally-occurring target molecule of a 53010 protein (e.g., a 53010 substrate or receptor), a 53010 antibody, a 53010 agonist or antagonist, a peptidomimetic of a 53010 agonist or antagonist, or other small molecule.

In one embodiment, the agent stimulates one or 53010 activities. Examples of such stimulatory agents include active 53010 protein and a nucleic acid molecule encoding 53010. In another embodiment, the agent inhibits one or more 53010 activities. Examples of such inhibitory agents include antisense 53010 nucleic acid molecules, anti-53010 antibodies, and 53010 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 53010 protein or nucleic acid molecule. In one embodiment, the method involves administering an agent (e.g., an agent identified by a screening assay described herein), or combination of agents that modulates (e.g., up regulates or down regulates) 53010 expression or activity. In another embodiment, the method involves administering a 53010 protein or nucleic acid molecule as therapy to compensate for reduced, aberrant, or unwanted 53010 expression or activity.

Stimulation of 53010 activity is desirable in situations in which 53010 is abnormally downregulated and/or in which increased 53010 activity is likely to have a beneficial effect. For example, stimulation of 53010 activity is desirable in situations in which a 53010 is downregulated and/or in which increased 53010 activity is likely to have a beneficial effect. Likewise, inhibition of 53010 activity is desirable in situations in which 53010 is abnormally upregulated and/or in which decreased 53010 activity is likely to have a beneficial effect.

Pharmacogenomics

The 53010 molecules of the present invention, as well as agents, or modulators which have a stimulatory or inhibitory effect on 53010 activity (e.g., 53010 gene expression) as identified by a screening assay described herein can be administered to individuals to treat (prophylactically or therapeutically) 53010 associated disorders (e.g., pain or a pain-related disorder) associated with aberrant or unwanted 53010 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a 53010 molecule or 53010 modulator as well as tailoring the dosage and/or therapeutic regimen of treatment with a 53010 molecule or 53010 modulator.

Pharmacogenomics deals with clinically significant hereditary variations in the response to drugs due to altered drug disposition and abnormal action in affected persons. See, for example, Eichelbaum, M. et al. (1996) Clin. Exp. Pharmacol. Physiol. 23:983–985 and Linder, M. W. et al. (1997) Clin. Chem. 43:254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach," can be utilized to identify genes that predict drug response. According to this method, if a gene that encodes a drug's target is known (e.g., a 53010 protein of the present invention), all common variants of that gene can be fairly easily identified in the population and it can be determined if having one version of the gene versus another is associated with a particular drug response.

Alternatively, a method termed the "gene expression profiling," can be utilized to identify genes that predict drug response. For example, the gene expression of an animal dosed with a drug (e.g., a 53010 molecule or 53010 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 53010 molecule or 53010 modulator, such as a modulator identified by one of the exemplary screening assays described herein.

The present invention further provides methods for identifying new agents, or combinations, that are based on identifying agents that modulate the activity of one or more of the gene products encoded by one or more of the 53010 genes of the present invention, wherein these products may be associated with resistance of the cells to a therapeutic agent. Specifically, the activity of the proteins encoded by the 53010 genes of the present invention can be used as a basis for identifying agents for overcoming agent resistance.

By blocking the activity of one or more of the resistance proteins, target cells, e.g., human cells, will become sensitive to treatment with an agent that the unmodified target cells were resistant to.

Monitoring the influence of agents (e.g., drugs) on the expression or activity of a 53010 protein can be applied in clinical trials. For example, the effectiveness of an agent determined by a screening assay as described herein to increase 53010 gene expression, protein levels, or upregulate 53010 activity, can be monitored in clinical trials of subjects exhibiting decreased 53010 gene expression, protein levels, or downregulated 53010 activity. Alternatively, the effectiveness of an agent determined by a screening assay to decrease 53010 gene expression, protein levels, or downregulate 53010 activity, can be monitored in clinical trials of subjects exhibiting increased 53010 gene expression, protein levels, or upregulated 53010 activity. In such clinical trials, the expression or activity of a 53010 gene, and preferably, other genes that have been implicated in, for example, a 53010-associated disorder can be used as a "read out" or markers of the phenotype of a particular cell.

53010 Informatics

The sequence of a 53010 molecule is provided in a variety of media to facilitate use thereof. A sequence can be provided as a manufacture, other than an isolated nucleic acid or amino acid molecule, which contains a 53010. Such a manufacture can provide a nucleotide or amino acid sequence, e.g., an open reading frame, in a form which allows examination of the manufacture using means not directly applicable to examining the nucleotide or amino acid sequences, or a subset thereof, as they exists in nature or in purified form. The sequence information can include, but is not limited to, 53010 full-length nucleotide and/or amino acid sequences, partial nucleotide and/or amino acid sequences, polymorphic sequences including single nucleotide polymorphisms (SNPs), epitope sequence, and the like. In a preferred embodiment, the manufacture is a machine-readable medium, e.g., a magnetic, optical, chemical or mechanical information storage device.

As used herein, "machine-readable media" refers to any medium that can be read and accessed directly by a machine, e.g., a digital computer or analogue computer. Non-limiting examples of a computer include a desktop PC, laptop, mainframe, server (e.g., a web server, network server, or server farm), handheld digital assistant, pager, mobile telephone, and the like. The computer can be stand-alone or connected to a communications network, e.g., a local area network (such as a VPN or intranet), a wide area network (e.g., an Extranet or the Internet), or a telephone network (e.g., a wireless, DSL, or ISDN network). Machine-readable media include, but are not limited to: magnetic storage media, such as floppy discs, hard disc storage medium, and magnetic tape; optical storage media such as CD-ROM; electrical storage media such as RAM, ROM, EPROM, EEPROM, flash memory, and the like; and hybrids of these categories such as magnetic/optical storage media.

A variety of data storage structures are available to a skilled artisan for creating a machine-readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

In a preferred embodiment, the sequence information is stored in a relational database (such as Sybase or Oracle). The database can have a first table for storing sequence (nucleic acid and/or amino acid sequence) information. The sequence information can be stored in one field (e.g., a first column) of a table row and an identifier for the sequence can be store in another field (e.g., a second column) of the table row. The database can have a second table, e.g., storing annotations. The second table can have a field for the sequence identifier, a field for a descriptor or annotation text (e.g., the descriptor can refer to a functionality of the sequence, a field for the initial position in the sequence to which the annotation refers, and a field for the ultimate position in the sequence to which the annotation refers. Non-limiting examples for annotation to nucleic acid sequences include polymorphisms (e.g., SNP's) translational regulatory sites and splice junctions. Non-limiting examples for annotations to amino acid sequence include polypeptide domains, e.g., a domain described herein; active sites and other functional amino acids; and modification sites.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention which match a particular target sequence or target motif. The search can be a BLAST search or other routine sequence comparison, e.g., a search described herein.

Thus, in one aspect, the invention features a method of analyzing 53010, e.g., analyzing structure, function, or relatedness to one or more other nucleic acid or amino acid sequences. The method includes: providing a 53010 nucleic acid or amino acid sequence; comparing the 53010 sequence with a second sequence, e.g., one or more preferably a plurality of sequences from a collection of sequences, e.g., a nucleic acid or protein sequence database to thereby analyze 53010. The method can be performed in a machine, e.g., a computer, or manually by a skilled artisan.

The method can include evaluating the sequence identity between a 53010 sequence and a database sequence. The method can be performed by accessing the database at a second site, e.g., over the Internet.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a 53010 sequence which includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features, a method of analyzing a sequence. The method includes: providing a 53010 sequence, or record, in machine-readable form; comparing a second sequence to the 53010 sequence; thereby analyzing a sequence. Comparison can include comparing to sequences for sequence identity or determining if one sequence is included within the other, e.g., determining if the 53010 sequence includes a sequence being compared. In a preferred embodiment the 53010 or second sequence is stored on a first computer, e.g., at a first site and the comparison is performed, read, or recorded on a second computer, e.g., at a second site. E.g., the 53010 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention provides a machine-readable medium for holding instructions for performing a method for determining whether a subject has a 53010-associated disease or disorder or a pre-disposition to a 53010-associated disease or disorder, wherein the method comprises the steps of determining 53010 sequence information associated with the subject and based on the 53010 sequence information, determining whether the subject has a 53010-associated disease or disorder or a pre-disposition to a 53010-associated disease or disorder and/or recommending a particular treatment for the disease, disorder or pre-disease condition.

The invention further provides in an electronic system and/or in a network, a method for determining whether a subject has a 53010-associated disease or disorder or a pre-disposition to a disease associated with a 53010 wherein the method comprises the steps of determining 53010 sequence information associated with the subject, and based on the 53010 sequence information, determining whether the subject has a 53010-associated disease or disorder or a pre-disposition to a 53010-associated disease or disorder, and/or recommending a particular treatment for the disease, disorder or pre-disease condition. In a preferred embodiment, the method further includes the step of receiving information, e.g., phenotypic or genotypic information, associated with the subject and/or acquiring from a network phenotypic information associated with the subject. The information can be stored in a database, e.g., a relational database. In another embodiment, the method further includes accessing the database, e.g., for records relating to other subjects, comparing the 53010 sequence of the subject to the 53010 sequences in the database to thereby determine whether the subject as a 53010-associated disease or disorder, or a pre-disposition for such.

The present invention also provides in a network, a method for determining whether a subject has a 53010 associated disease or disorder or a pre-disposition to a 53010-associated disease or disorder associated with 53010, said method comprising the steps of receiving 53010 sequence information from the subject and/or information related thereto, receiving phenotypic information associated with the subject, acquiring information from the network corresponding to 53010 and/or corresponding to a 53010-associated disease or disorder (e.g., pain or a pain-related disorder), and based on one or more of the phenotypic information, the 53010 information (e.g., sequence information and/or information related thereto), and the acquired information, determining whether the subject has a 53010-associated disease or disorder or a pre-disposition to a 53010-associated disease or disorder. The method may further comprise the step of recommending a particular treatment for the disease, disorder or pre-disease condition.

The present invention also provides a method for determining whether a subject has a 53010-associated disease or disorder or a pre-disposition to a 53010-associated disease or disorder, said method comprising the steps of receiving information related to 53010 (e.g., sequence information and/or information related thereto), receiving phenotypic information associated with the subject, acquiring information from the network related to 53010 and/or related to a 53010-associated disease or disorder, and based on one or more of the phenotypic information, the 53010 information, and the acquired information, determining whether the subject has a 53010-associated disease or disorder or a pre-disposition to a 53010-associated disease or disorder. The method may further comprise the step of recommending a particular treatment for the disease, disorder or pre-disease condition.

This invention is further illustrated by the following examples that should not be construed as limiting. The contents of all references, patents and published patent applications cited throughout this application are incorporated herein by reference.

EXAMPLES

Example 1

Identification and Characterization of Human 53010 cDNA

The human 53010 nucleic acid sequence is recited as follows:

CCACGCGTCCGAAAAACAGGCCTGGAGAGCAATGTGGAGTAAGCAATGTAA (SEQ ID NO:1).
TAAAAACGATTTAAAAATTATTCTTAATAAAAGTACGAATCCCATGCCACA
GGGACTTACTTCATCTGCTTCACAATGGTGCTTTTTCCTGATTCTCCAGCCCCT
GTTGGGACACAGACAGTGGGGAAAAACTGGGCCTTCTGCTGAAGGGCCACA
GAGGAACACCAGGCTGGGATGGATTCAGGGCAAGCAAGTCACTGTGCTGGG
AAGCCCTGTGCCTGTGAACGTGTTCCTCGGAGTCCCCTTTGCTGCTCCCCGC
TGGGATCCCTGCGATTTACGAACCCGCAGCCTGCATCGCCCTGGGATAACTT
GCGAGAAGCCACCTCCTACCCTAATTTGTGCCTCCAGAACTCAGAGTGGCTG
CTCTTAGATCAACACATGCTCAAGGTGCATTACCCGAAATTCGGAGTGTCAG
AAGACTGCCTCTACCTGAACATCTATGCGCCTGCCCACGCCGATACAGGCTC
CAAGCTCCCCGTCTTGGTGTGGTTCCCAGGAGGTGCCTTCAAGACTGGCTCAG
CCTCCATCTTTGATGGGTCCGCCCTGGCTGCCTATGAGGACGTGCTGGTTGTG
GTCGTCCAGTACCGGCTAGGAATATTTGGTTTCTTCACCACATGGGATCAGCA
TGCTCCGGGGAACTGGGCCTTCAAGGACCAGGTGGCTGCTCTGTCCTGGGTC
CAGAAGAACATCGAGTTCTTCGGTGGGACCCCAGCTCTGTGACCATCTTTG
GCGAGTCCGCGGGAGCCATAAGTGTTTCTAGTCTTATACTGTCTCCCATGGCC
AAAGGCTTATTCCACAAAGCCATCATGGAGAGTGGGGTGGCCATCATCCCTT
ACCTGGAGGCCCATGATTATGAGAAGAGTGAGGACCTGCAGGTGGTTGCACA
TTTCTGTGGTAACAATGCGTCAGACTCTGAGGCCCTGCTGAGGTGCCTGAGG
ACAAAACCCTCCAAGGAGCTGCTGACCCTCAGCCAGAAAACAAAGTCTTTCA
CTCGAGTGGTTGATGGTGCTTTCTTTCCTAATGAGCCTCTAGATCTATTGTCTC
AGAAAGCATTTAAAGCAATTCCTTCCATCATCGGAGTCAATAACCACGAGTG
TGGCTTCCTGCTGCCTATGAAGGAGGCTCCTGAGATCCTCAGTGGCTCCAACA
AGTCCCTTGCCCTCCATCTGATACAAAACATCCTGCACATCCCGCCTCAGTAT
TTGCACCTTGTGGCTAATGAATACTTCCATGACAAGCACTCCCTGACTGAAAT
CCGAGACAGTCTTCTGGACTTGCTTGGAGATGTGTTCTTTGTGGTCCCTGCAC
TGATCACAGCTCGATATCACAGAGATGCTGGTGCACCTGTCTACTTCTATGAG
TTTCGGCACCGGCCTCAGTGCTTTGAAGACACGAAGCCGGCTTTTGTCAAAGC
CGACCACGCTGATGAAGTCCGCTTTGTGTTCGGTGGTGCCTTCCTGAAGGGGG
ACATTGTTATGTTCGAAGGAGCCACGGAGGAGGAGAAGTTACTGAGCCGGAA
GATGATGAAATACTGGGCTACCTTTGCTCGAACCGGGAATCCTAATGGGAAC
GACCTGTCTCTGTGGCCAGCTTATAATCTGACTGAGCAGTACCTCCAGCTGGA
CTTGAACATGAGCCTCGGACAGAGACTCAAAGAACCGCGGGTGGATTTTTGG
ACCAGCACCATCCCCCTGATCCTGTCTGCCTCCGACATGCTCCACAGTCCTCT
TTCTTCCTTAACTTTCCTCTCTCTCCTCCAGCCTTTCTTTTTCTTTTGTGCTCCT
TGAGAAGTTATCTTTCTGTGATTTTGGTTTCCCTTCTCCTCCCATAATTTCTCC
CGCAATCATTAGCTTCTTTCTGAGCTCAGCTGCTTTCTATGGGATCCTTGCA
AAACAAGCTGCTTTCGCTGATATTTTATGGACTTAGGAATGATCCTTACAGAA
TTCTTTTCAACATCAAAAAGTGCAATTTGTCTTGGAAGGCAACAAGATTTCTT

-continued
CAATAAATTTGGAAGAGGGCTGGCCTATTAGTTGTCATAATAATGGTTTTGTA

ACTCATATGAAATAAAATCAGAATGTAAAATAGGAAAAAAAAAAAAAAAAA

AAA.

The human 53010 sequence (SEQ ID NO: 1) is approximately 2158 nucleotides long. The nucleic acid sequence includes an initiation codon (ATG) and a termination codon (TGA) which are underscored above. The region between and inclusive of the initiation codon and the termination codon is a methionine-initiated coding sequence of about 1746 nucleotides, including the termination codon (nucleotides indicated as "coding" of SEQ ID NO:1; SEQ ID NO:3). The coding sequence encodes a 581 amino acid protein (SEQ ID NO:2), which is recited as follows:

MPQGLTSSASQWCFFLILQPLLGHRQWGKTGPSAEGPQRNTRLGWIQGKQVTVL

GSPVPVNVFLGVPFAAPPLGSLRFTNPQPASPWDNLREATSYPNLCLQNSEWLLL

DQHMLKVHYPKFGVSEDCLYLNIYAPAHADTGSKLPVLVWFPGGAFKTGSASIF

DGSALAAYEDVLVVVVQYRLGIFGFFTTWDQHAPGNWAFKDQVAALSWVQKN

IEFFGGDPSSVTIFGESAGAISVSSLILSPMAKGLFHKAIMESGVAIIPYLEAHDYEK

SEDLQVVAHFCGNNASDSEALLRCLRTKPSKELLTLSQKTKSFTRVVDGAFFPNE

PLDLLSQKAFKAIPSIIGVNNHECGFLLPMKEAPEILSGSNKSLALHLIQNILHIPPQ

YLHLVANEYFHDKHSLTEIRDSLLDLLGDVFFVVPALITARYHRDAGAPVYFYEF

RHRPQCFEDTKPAFVKADHADEVRFVFGGAFLKGDIVMFEGATEEEKLLSRKM

MKYWATFARTGNPNGNDLSLWPAYNLTEQYLQLDLNMSLGQRLKEPRVDFWT

STIPLILSASDMLHSPLSSLTFLSLLQPFFFFCAP.

(SEQ ID NO:2).

RNA using an oligo-dT primer and Superscript II reverse transcriptase (Gibco/BRL). cDNA obtained from approximately 50 ng total RNA was used per TaqMan reaction. Tissues tested include the human tissues and several cell lines shown in Tables 1–3. As shown in Table 1, 53010 mRNA was detected in brain, spinal cord, dorsal root ganglion (DRG), and kidney. As shown in Table 2, 53010 mRNA was detected in testes, brain, spinal cord, dorsal root ganglion (DRG), skin, and liver. As shown in Table 3, 53010 mRNA was detected in brain, spinal cord, dorsal root ganglion (DRG), and superior cervical ganglion (SCG).

Example 2

Tissue Distribution of 53010 mRNA by TaqMan Analysis

Endogenous human 53010 gene expression was determined using the Perkin-Elmer/ABI 7700 Sequence Detection System which employs TaqMan technology. Briefly, TaqMan technology relies on standard RT-PCR with the addition of a third gene-specific oligonucleotide (referred to as a probe) which has a fluorescent dye coupled to its 5' end (typically 6-FAM) and a quenching dye at the 3' end (typically TAMRA). When the fluorescently tagged oligonucleotide is intact, the fluorescent signal from the 5' dye is quenched. As PCR proceeds, the 5' to 3' nucleolytic activity of Taq polymerase digests the labeled primer, producing a free nucleotide labeled with 6-FAM, which is now detected as a fluorescent signal. The PCR cycle where fluorescence is first released and detected is directly proportional to the starting amount of the gene of interest in the test sample, thus providing a quantitative measure of the initial template concentration. Samples can be internally controlled by the addition of a second set of primers/probe specific for a housekeeping gene such as GAPDH which has been labeled with a different fluorophore on the 5' end (typically VIC).

To determine the level of 53010 in various human tissues a primer/probe set was designed. Total RNA was prepared from a series of human tissues using an RNeasy kit from Qiagen. First strand cDNA was prepared from 1 μg total

TABLE 1

Expression of 53010

| Tissue Type | Relative Expression |
| --- | --- |
| Artery normal | 0 |
| Aorta diseased | 0 |
| Vein normal | 0 |
| Coronary Smooth Muscle Cells | 0 |
| Human Umbilical Vein Endothelial Cells | 0 |
| Hemangioma | 0 |
| Heart normal | 0 |
| Heart congestive heart failure | 0 |
| Kidney | 1.4298 |
| Skeletal Muscle | 0 |
| Adipose normal | 0 |
| Pancreas | 0 |
| primary osteoblasts | 0 |
| Osteoclasts (diff) | 0 |
| Skin normal | 0 |
| Spinal cord normal | 0.9143 |
| Brain Cortex normal | 16.4588 |
| Brain Hypothalamus normal | 0 |
| Nerve | 0 |
| Dorsal Root Ganglion | 1.1102 |
| Breast normal | 0 |
| Breast tumor | 0 |
| Ovary normal | 0 |
| Ovary Tumor | 0 |
| Prostate Normal | 0 |

TABLE 1-continued

Expression of 53010

| Tissue Type | Relative Expression |
| --- | --- |
| Prostate Tumor | 0 |
| Salivary glands | 0 |
| Colon normal | 0 |
| Colon Tumor | 0 |
| Lung normal | 0 |
| Lung tumor | 0 |
| Lung Chronic Obstructive Pulmonary Disease | 0 |
| Colon Inflammatory Bowel Disease | 0 |
| Liver normal | 0 |
| Liver fibrosis | 0 |
| Spleen normal | 0 |
| Tonsil normal | 0.0466 |
| Lymph node normal | 0 |
| Small intestine normal | 0 |
| Macrophages | 0 |
| Synovium | 0 |
| Bone Marrow, Mononuclear Cells | 0 |
| Activated peripheral blood mononuclear cells | 0 |
| Neutrophils | 0 |
| Megakaryocytes | 0 |
| Erythroid | 0 |
| positive control | 18.5171 |

TABLE 2

Expression of 53010 in Human Tissues

| Tissue Type | Relative Expression |
| --- | --- |
| Adrenal Gland | 0.02 |
| Brain | 0.86 |
| Heart | 0.00 |
| Kidney | 0.01 |
| Liver | 0.14 |
| Lung | 0.00 |
| Mammary Gland | 0.00 |
| Pancreas | 0.01 |
| Placenta | 0.00 |
| Prostate | 0.01 |
| Salivary Gland | 0.01 |
| Muscle | 0.01 |
| Small Intestine | 0.00 |
| Spleen | 0.00 |
| Stomach | 0.01 |
| Testes | 3.30 |
| Thymus | 0.02 |
| Trachea | 0.06 |
| Uterus | 0.00 |
| Spinal Cord | 0.25 |
| DRG | 0.07 |
| Skin | 0.22 |

TABLE 3

Expression of 53010 in Rat Tissues

| Tissue | Relative Expression |
| --- | --- |
| Brain | 0.006 |
| Spinal Cord | 0.012 |
| Dorsal Root Ganglia | 0.008 |
| Superior Cervical Ganglion | 0.002 |
| Hairy Skin | 0.000 |
| Gastro Muscle | 0.000 |
| Heart | 0.000 |
| Kidney | 0.000 |
| Liver | 0.000 |
| Lung | 0.000 |
| Spleen | 0.000 |
| Aorta | 0.000 |

TABLE 3-continued

Expression of 53010 in Rat Tissues

| Tissue | Relative Expression |
| --- | --- |
| Adrenal Gland | 0.000 |
| Salivary Gland | 0.000 |
| Thyroid | 0.000 |
| Prostate | 0.000 |
| Thymus | 0.000 |
| Trachea | 0.000 |
| Esophagus | 0.000 |
| Duodenum | 0.000 |
| Diaphragm | 0.000 |

The regulation of the rat orthologue of the 53010 gene was evaluated in rodent models of pain response. In these experiments, 53010 expression was evaluated at various days (D) following the treatment. Table 4 shows the regulation of 53010 expression in dorsal root ganglion (DRG) following CFA injection (days 1, 3, 7, 14, and 28), axotomy (AX; days 1, 3, 7, 14, and 28), and CCI (days 3, 7, 10, 14, and 28). Table 5 shows the regulation of 53010 expression in the spinal cord (SC) following CFA injection (days 3, 7, 14, and 28), axotomy (AX; days 1, 3, 7, 14, and 28), and CCI (days 3, 7, and 14).

TABLE 4

Regulation of 53010 Expression in Dorsal Root Ganglion

| Sample | Relative Expression |
| --- | --- |
| Naïve DRG | 0.00562389 |
| CCI D3, ipsilateral, DRG | 0.00349809 |
| CCI D7, ipsilateral, DRG | 0.00397669 |
| CCI D10, ipsilateral, DRG | 0.00421803 |
| CCI D14, ipsilateral, DRG | 0.00280222 |
| CCI D28, ipsilateral, DRG | 0.00228401 |
| Naïve DRG | 0.00562389 |
| CFA D1 ipsilateral, DRG | 0.00192062 |
| CFA D3 ipsilateral, DRG | 0.00408849 |
| CFA D7 ipsilateral, DRG | 0.00226039 |
| CFA D14 ipsilateral, DRG | 0.00227611 |
| CFA D28 ipsilateral, DRG | 0.00588307 |
| Naïve DRG | 0.00562389 |
| AX D1, ipsilateral, DRG | 0.00267877 |
| AX D3, ipsilateral, DRG | 0.00173696 |
| AX D7, ipsilateral, DRG | 0.00266026 |
| AX D14, ipsilateral, DRG | 0.00118228 |
| AX D28, ipsilateral, DRG | 0.00421803 |

TABLE 5

Regulation of 53010 Expression in Spinal Cord

| Sample | Relative Expression |
| --- | --- |
| Naïve SC | 0.00394922 |
| CCI D3, ipsilateral, SC | 0.00438194 |
| CCI D7, ipsilateral, SC | 0.00496423 |
| CCI D14, ipsilateral, SC | 0.01109293 |
| Naïve SC | 0.00394922 |
| CFA D3 ipsilateral, SC | 0.00400435 |
| CFA D7 ipsilateral, SC | 0.00843606 |
| CFA D14 ipsilateral, SC | 0.00162627 |
| CFA D28 ipsilateral, SC | 0.00530212 |
| Naïve SC | 0.00739509 |
| AX D1, ipsilateral, SC | 0.00721785 |

TABLE 5-continued

Regulation of 53010 Expression in Spinal Cord

| Sample | Relative Expression |
|---|---|
| AX D3, ipsilateral, SC | 0.006876 |
| AX D7, ipsilateral, SC | 0.00843606 |
| AX D14, ipsilateral, SC | 0.00426211 |
| AX D28, ipsilateral, SC | 0.00359644 |

Example 3

Tissue Distribution of 53010 mRNA by Northern Analysis

Northern blot hybridizations with various RNA samples can be performed under standard conditions and washed under stringent conditions, i.e., 0.2× SSC at 65° C. A DNA probe corresponding to all or a portion of the 53010 cDNA (SEQ ID NO:1) can be used. The DNA was radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 4

Recombinant Expression of 53010 in Bacterial Cells

In this example, 53010 is expressed as a recombinant glutathione-S-transferase (GST) fusion polypeptide in *E. coli* and the fusion polypeptide is isolated and characterized. Specifically, 53010 is fused to GST and this fusion polypeptide is expressed in *E. coli*, e.g., strain PEB199. Expression of the GST-53010 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 5

Expression of Recombinant 53010 Protein in COS Cells

To express the 53010 gene in COS cells (e.g., COS-7 cells, CV-1 origin SV40 cells; Gluzman (1981) *Cell* 23:175–182), the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 53010 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 53010 DNA sequence is amplified by PCR using two primers. The 5' primer contains the restriction site of interest followed by approximately twenty nucleotides of the 53010 coding sequence starting from the initiation codon; the 3' end sequence contains complementary sequences to the other restriction site of interest, a translation stop codon, the HA tag or FLAG tag and the last 20 nucleotides of the 53010 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the 53010 gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 53010-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. (1989) *Molecular Cloning: A Laboratory Manual. 2nd, ed. Cold Spring Harbor Laboratory*, Cold Spring Harbor Laboratory Press, Cold Spring Harbor, N.Y. The expression of the 53010 polypeptide is detected by radiolabelling ($^{35}$S-methionine or $^{35}$S-cysteine available from NEN, Boston, Mass., can be used) and immunoprecipitation (Harlow, E. and Lane, D. (1988) *Antibodies: A Laboratory Manual*, Cold Spring Harbor Laboratory Press, Cold Spring Harbor, N.Y.) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 53010 coding sequence is cloned directly into the polylinker of the pCDNA/Amp vector using the appropriate restriction sites. The resulting plasmid is transfected into COS cells in the manner described above, and the expression of the 53010 polypeptide is detected by radiolabelling and immunoprecipitation using a 53010 specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid molecule selected from the group consisting of:

a) a nucleic acid comprising the nucleotide sequence of SEQ ID NO:1, SEQ ID NO:3, or a full complement thereof; and b) a nucleic acid molecule which encodes a polypeptide comprising the amino acid sequence of SEQ ID NO:2.

2. The nucleic acid molecule of claim 1, further comprising vector nucleic acid sequences.

3. The nucleic acid molecule of claim 1, further comprising nucleic acid sequences encoding a heterologous polypeptide.

4. A host cell which contains the nucleic acid molecule of claim 1.

5. A method for producing a polypeptide comprising the amino acid sequence of SEQ ID NO:2, the method comprising culturing the host cell of claim 4 under conditions in which the nucleic acid molecule is expressed.

\* \* \* \* \*

SEQUENCE LISTING

<160> NUMBER OF SEQ ID NOS: 6

<210> SEQ ID NO 1
<211> LENGTH: 2158
<212> TYPE: DNA
<213> ORGANISM: Homo sapiens
<220> FEATURE:
<221> NAME/KEY: CDS
<222> LOCATION: (96)...(1838)

<400> SEQUENCE: 1

```
ccacgcgtcc gaaaaacagg cctggagagc aatgtggagt aagcaatgta ataaaaacga       60
tttaaaaatt attcttaata aaagtacgaa tccca atg cca cag gga ctt act          113
                                      Met Pro Gln Gly Leu Thr
                                        1               5 tca tct gct tca caa tgg tgc ttt ttc ctg att ctc cag ccc ctg ttg         161
Ser Ser Ala Ser Gln Trp Cys Phe Phe Leu Ile Leu Gln Pro Leu Leu
            10                  15                  20 gga cac aga cag tgg gga aaa act ggg cct tct gct gaa ggg cca cag         209
Gly His Arg Gln Trp Gly Lys Thr Gly Pro Ser Ala Glu Gly Pro Gln
        25                  30                  35 agg aac acc agg ctg gga tgg att cag ggc aag caa gtc act gtg ctg         257
Arg Asn Thr Arg Leu Gly Trp Ile Gln Gly Lys Gln Val Thr Val Leu
    40                  45                  50 gga agc cct gtg cct gtg aac gtg ttc ctc gga gtc ccc ttt gct gct         305
Gly Ser Pro Val Pro Val Asn Val Phe Leu Gly Val Pro Phe Ala Ala
55                  60                  65                  70 ccc ccg ctg gga tcc ctg cga ttt acg aac ccg cag cct gca tcg ccc         353
Pro Pro Leu Gly Ser Leu Arg Phe Thr Asn Pro Gln Pro Ala Ser Pro
                75                  80                  85 tgg gat aac ttg cga gaa gcc acc tcc tac cct aat ttg tgc ctc cag         401
Trp Asp Asn Leu Arg Glu Ala Thr Ser Tyr Pro Asn Leu Cys Leu Gln
            90                  95                 100 aac tca gag tgg ctg ctc tta gat caa cac atg ctc aag gtg cat tac         449
Asn Ser Glu Trp Leu Leu Leu Asp Gln His Met Leu Lys Val His Tyr
        105                 110                 115 ccg aaa ttc gga gtg tca gaa gac tgc ctc tac ctg aac atc tat gcg         497
Pro Lys Phe Gly Val Ser Glu Asp Cys Leu Tyr Leu Asn Ile Tyr Ala
    120                 125                 130 cct gcc cac gcc gat aca ggc tcc aag ctc ccc gtc ttg gtg tgg ttc         545
Pro Ala His Ala Asp Thr Gly Ser Lys Leu Pro Val Leu Val Trp Phe
135                 140                 145                 150 cca gga ggt gcc ttc aag act ggc tca gcc tcc atc ttt gat ggg tcc         593
Pro Gly Gly Ala Phe Lys Thr Gly Ser Ala Ser Ile Phe Asp Gly Ser
                155                 160                 165 gcc ctg gct gcc tat gag gac gtg ctg gtt gtg gtc cag tac cgg              641
Ala Leu Ala Ala Tyr Glu Asp Val Leu Val Val Val Gln Tyr Arg
            170                 175                 180 cta gga ata ttt ggt ttc ttc acc aca tgg gat cag cat gct ccg ggg         689
Leu Gly Ile Phe Gly Phe Phe Thr Thr Trp Asp Gln His Ala Pro Gly
        185                 190                 195 aac tgg gcc ttc aag gac cag gtg gct gct ctg tcc tgg gtc cag aag         737
Asn Trp Ala Phe Lys Asp Gln Val Ala Ala Leu Ser Trp Val Gln Lys
    200                 205                 210 aac atc gag ttc ttc ggt ggg gac ccc agc tct gtg acc atc ttt ggc         785
Asn Ile Glu Phe Phe Gly Gly Asp Pro Ser Ser Val Thr Ile Phe Gly
215                 220                 225                 230 gag tcc gcg gga gcc ata agt gtt tct agt ctt ata ctg tct ccc atg         833
Glu Ser Ala Gly Ala Ile Ser Val Ser Ser Leu Ile Leu Ser Pro Met
```

-continued

|  |  |  |  |  |  |  |  |  |  |  |  |  |  |  |  |
|---|---|---|---|---|---|---|---|---|---|---|---|---|---|---|---|
|  |  |  | 235 |  |  |  | 240 |  |  |  | 245 |  |  |  |  |
| gcc | aaa | ggc | tta | ttc | cac | aaa | gcc | atc | atg | gag | agt | ggg | gtg | gcc | atc | 881 |
| Ala | Lys | Gly | Leu | Phe | His | Lys | Ala | Ile | Met | Glu | Ser | Gly | Val | Ala | Ile |  |
|  |  |  | 250 |  |  |  | 255 |  |  |  | 260 |  |  |  |  |  |
| atc | cct | tac | ctg | gag | gcc | cat | gat | tat | gag | aag | agt | gag | gac | ctg | cag | 929 |
| Ile | Pro | Tyr | Leu | Glu | Ala | His | Asp | Tyr | Glu | Lys | Ser | Glu | Asp | Leu | Gln |  |
|  |  | 265 |  |  |  |  | 270 |  |  |  |  | 275 |  |  |  |  |
| gtg | gtt | gca | cat | ttc | tgt | ggt | aac | aat | gcg | tca | gac | tct | gag | gcc | ctg | 977 |
| Val | Val | Ala | His | Phe | Cys | Gly | Asn | Asn | Ala | Ser | Asp | Ser | Glu | Ala | Leu |  |
|  | 280 |  |  |  |  | 285 |  |  |  |  | 290 |  |  |  |  |  |
| ctg | agg | tgc | ctg | agg | aca | aaa | ccc | tcc | aag | gag | ctg | ctg | acc | ctc | agc | 1025 |
| Leu | Arg | Cys | Leu | Arg | Thr | Lys | Pro | Ser | Lys | Glu | Leu | Leu | Thr | Leu | Ser |  |
| 295 |  |  |  |  | 300 |  |  |  |  | 305 |  |  |  |  | 310 |  |
| cag | aaa | aca | aag | tct | ttc | act | cga | gtg | gtt | gat | ggt | gct | ttc | ttt | cct | 1073 |
| Gln | Lys | Thr | Lys | Ser | Phe | Thr | Arg | Val | Val | Asp | Gly | Ala | Phe | Phe | Pro |  |
|  |  |  |  | 315 |  |  |  |  | 320 |  |  |  |  | 325 |  |  |
| aat | gag | cct | cta | gat | cta | ttg | tct | cag | aaa | gca | ttt | aaa | gca | att | cct | 1121 |
| Asn | Glu | Pro | Leu | Asp | Leu | Leu | Ser | Gln | Lys | Ala | Phe | Lys | Ala | Ile | Pro |  |
|  |  |  | 330 |  |  |  | 335 |  |  |  | 340 |  |  |  |  |  |
| tcc | atc | atc | gga | gtc | aat | aac | cac | gag | tgt | ggc | ttc | ctg | ctg | cct | atg | 1169 |
| Ser | Ile | Ile | Gly | Val | Asn | Asn | His | Glu | Cys | Gly | Phe | Leu | Leu | Pro | Met |  |
|  |  | 345 |  |  |  |  | 350 |  |  |  |  | 355 |  |  |  |  |
| aag | gag | gct | cct | gag | atc | ctc | agt | ggc | tcc | aac | aag | tcc | ctt | gcc | ctc | 1217 |
| Lys | Glu | Ala | Pro | Glu | Ile | Leu | Ser | Gly | Ser | Asn | Lys | Ser | Leu | Ala | Leu |  |
|  | 360 |  |  |  |  | 365 |  |  |  |  | 370 |  |  |  |  |  |
| cat | ctg | ata | caa | aac | atc | ctg | cac | atc | ccg | cct | cag | tat | ttg | cac | ctt | 1265 |
| His | Leu | Ile | Gln | Asn | Ile | Leu | His | Ile | Pro | Pro | Gln | Tyr | Leu | His | Leu |  |
| 375 |  |  |  |  | 380 |  |  |  |  | 385 |  |  |  |  | 390 |  |
| gtg | gct | aat | gaa | tac | ttc | cat | gac | aag | cac | tcc | ctg | act | gaa | atc | cga | 1313 |
| Val | Ala | Asn | Glu | Tyr | Phe | His | Asp | Lys | His | Ser | Leu | Thr | Glu | Ile | Arg |  |
|  |  |  |  | 395 |  |  |  |  | 400 |  |  |  |  | 405 |  |  |
| gac | agt | ctt | ctg | gac | ttg | ctt | gga | gat | gtg | ttc | ttt | gtg | gtc | cct | gca | 1361 |
| Asp | Ser | Leu | Leu | Asp | Leu | Leu | Gly | Asp | Val | Phe | Phe | Val | Val | Pro | Ala |  |
|  |  |  | 410 |  |  |  | 415 |  |  |  | 420 |  |  |  |  |  |
| ctg | atc | aca | gct | cga | tat | cac | aga | gat | gct | ggt | gca | cct | gtc | tac | ttc | 1409 |
| Leu | Ile | Thr | Ala | Arg | Tyr | His | Arg | Asp | Ala | Gly | Ala | Pro | Val | Tyr | Phe |  |
|  |  | 425 |  |  |  |  | 430 |  |  |  |  | 435 |  |  |  |  |
| tat | gag | ttt | cgg | cac | cgg | cct | cag | tgc | ttt | gaa | gac | acg | aag | ccg | gct | 1457 |
| Tyr | Glu | Phe | Arg | His | Arg | Pro | Gln | Cys | Phe | Glu | Asp | Thr | Lys | Pro | Ala |  |
|  | 440 |  |  |  |  | 445 |  |  |  |  | 450 |  |  |  |  |  |
| ttt | gtc | aaa | gcc | gac | cac | gct | gat | gaa | gtc | cgc | ttt | gtg | ttc | ggt | ggt | 1505 |
| Phe | Val | Lys | Ala | Asp | His | Ala | Asp | Glu | Val | Arg | Phe | Val | Phe | Gly | Gly |  |
| 455 |  |  |  |  | 460 |  |  |  |  | 465 |  |  |  |  | 470 |  |
| gcc | ttc | ctg | aag | ggg | gac | att | gtt | atg | ttc | gaa | gga | gcc | acg | gag | gag | 1553 |
| Ala | Phe | Leu | Lys | Gly | Asp | Ile | Val | Met | Phe | Glu | Gly | Ala | Thr | Glu | Glu |  |
|  |  |  |  | 475 |  |  |  |  | 480 |  |  |  |  | 485 |  |  |
| gag | aag | tta | ctg | agc | cgg | aag | atg | atg | aaa | tac | tgg | gct | acc | ttt | gct | 1601 |
| Glu | Lys | Leu | Leu | Ser | Arg | Lys | Met | Met | Lys | Tyr | Trp | Ala | Thr | Phe | Ala |  |
|  |  |  | 490 |  |  |  | 495 |  |  |  | 500 |  |  |  |  |  |
| cga | acc | ggg | aat | cct | aat | ggg | aac | gac | ctg | tct | ctg | tgg | cca | gct | tat | 1649 |
| Arg | Thr | Gly | Asn | Pro | Asn | Gly | Asn | Asp | Leu | Ser | Leu | Trp | Pro | Ala | Tyr |  |
|  |  | 505 |  |  |  |  | 510 |  |  |  |  | 515 |  |  |  |  |
| aat | ctg | act | gag | cag | tac | ctc | cag | ctg | gac | ttg | aac | atg | agc | ctc | gga | 1697 |
| Asn | Leu | Thr | Glu | Gln | Tyr | Leu | Gln | Leu | Asp | Leu | Asn | Met | Ser | Leu | Gly |  |
|  | 520 |  |  |  |  | 525 |  |  |  |  | 530 |  |  |  |  |  |
| cag | aga | ctc | aaa | gaa | ccg | cgg | gtg | gat | ttt | tgg | acc | agc | acc | atc | ccc | 1745 |
| Gln | Arg | Leu | Lys | Glu | Pro | Arg | Val | Asp | Phe | Trp | Thr | Ser | Thr | Ile | Pro |  |
| 535 |  |  |  |  | 540 |  |  |  |  | 545 |  |  |  |  | 550 |  |
| ctg | atc | ctg | tct | gcc | tcc | gac | atg | ctc | cac | agt | cct | ctt | tct | tcc | tta | 1793 |

```
Leu Ile Leu Ser Ala Ser Asp Met Leu His Ser Pro Leu Ser Ser Leu
                555                 560                 565 act ttc ctc tct ctc ctc cag cct ttc ttt ttc ttt tgt gct cct        1838
Thr Phe Leu Ser Leu Leu Gln Pro Phe Phe Phe Phe Cys Ala Pro
            570                 575                 580 tgagaagtta tctttctgtg attttggttt ccttctcct cccataattt ctcccgcaat    1898
cattagcttc tttctgagct cagctgcttt ctatggggat ccttgcaaaa caagctgctt   1958
tcgctgatat tttatggact taggaatgat ccttacagaa ttcttttcaa catcaaaaag   2018
tgcaatttgt cttggaaggc aacaagattt cttcaataaa tttggaagag ggctggccta   2078
ttagttgtca taataatggt tttgtaactc atatgaaata aaatcagaat gtaaaatagg   2138
aaaaaaaaaa aaaaaaaaaa                                               2158

<210> SEQ ID NO 2
<211> LENGTH: 581
<212> TYPE: PRT
<213> ORGANISM: Homo sapiens

<400> SEQUENCE: 2

Met Pro Gln Gly Leu Thr Ser Ser Ala Ser Gln Trp Cys Phe Phe Leu
  1               5                  10                  15

Ile Leu Gln Pro Leu Leu Gly His Arg Gln Trp Gly Lys Thr Gly Pro
             20                  25                  30

Ser Ala Glu Gly Pro Gln Arg Asn Thr Arg Leu Gly Trp Ile Gln Gly
         35                  40                  45

Lys Gln Val Thr Val Leu Gly Ser Pro Val Pro Val Asn Val Phe Leu
     50                  55                  60

Gly Val Pro Phe Ala Ala Pro Pro Leu Gly Ser Leu Arg Phe Thr Asn
 65                  70                  75                  80

Pro Gln Pro Ala Ser Pro Trp Asp Asn Leu Arg Glu Ala Thr Ser Tyr
                 85                  90                  95

Pro Asn Leu Cys Leu Gln Asn Ser Glu Trp Leu Leu Leu Asp Gln His
            100                 105                 110

Met Leu Lys Val His Tyr Pro Lys Phe Gly Val Ser Glu Asp Cys Leu
        115                 120                 125

Tyr Leu Asn Ile Tyr Ala Pro Ala His Ala Asp Thr Gly Ser Lys Leu
    130                 135                 140

Pro Val Leu Val Trp Phe Pro Gly Gly Ala Phe Lys Thr Gly Ser Ala
145                 150                 155                 160

Ser Ile Phe Asp Gly Ser Ala Leu Ala Ala Tyr Glu Asp Val Leu Val
                165                 170                 175

Val Val Val Gln Tyr Arg Leu Gly Ile Phe Gly Phe Phe Thr Thr Trp
            180                 185                 190

Asp Gln His Ala Pro Gly Asn Trp Ala Phe Lys Asp Gln Val Ala Ala
        195                 200                 205

Leu Ser Trp Val Gln Lys Asn Ile Glu Phe Phe Gly Gly Asp Pro Ser
    210                 215                 220

Ser Val Thr Ile Phe Gly Glu Ser Ala Gly Ala Ile Ser Val Ser Ser
225                 230                 235                 240

Leu Ile Leu Ser Pro Met Ala Lys Gly Leu Phe His Lys Ala Ile Met
                245                 250                 255

Glu Ser Gly Val Ala Ile Ile Pro Tyr Leu Glu Ala His Asp Tyr Glu
            260                 265                 270

Lys Ser Glu Asp Leu Gln Val Val Ala His Phe Cys Gly Asn Asn Ala
```

```
Ser Asp Ser Glu Ala Leu Leu Arg Cys Leu Arg Thr Lys Pro Ser Lys
    290                 295                 300
Glu Leu Leu Thr Leu Ser Gln Lys Thr Lys Ser Phe Thr Arg Val Val
305                 310                 315                 320
Asp Gly Ala Phe Phe Pro Asn Glu Pro Leu Asp Leu Leu Ser Gln Lys
                325                 330                 335
Ala Phe Lys Ala Ile Pro Ser Ile Ile Gly Val Asn Asn His Glu Cys
            340                 345                 350
Gly Phe Leu Leu Pro Met Lys Glu Ala Pro Glu Ile Leu Ser Gly Ser
        355                 360                 365
Asn Lys Ser Leu Ala Leu His Leu Ile Gln Asn Ile Leu His Ile Pro
370                 375                 380
Pro Gln Tyr Leu His Leu Val Ala Asn Glu Tyr Phe His Asp Lys His
385                 390                 395                 400
Ser Leu Thr Glu Ile Arg Asp Ser Leu Leu Asp Leu Leu Gly Asp Val
                405                 410                 415
Phe Phe Val Val Pro Ala Leu Ile Thr Ala Arg Tyr His Arg Asp Ala
            420                 425                 430
Gly Ala Pro Val Tyr Phe Tyr Glu Phe Arg His Arg Pro Gln Cys Phe
        435                 440                 445
Glu Asp Thr Lys Pro Ala Phe Val Lys Ala Asp His Ala Asp Glu Val
    450                 455                 460
Arg Phe Val Phe Gly Gly Ala Phe Leu Lys Gly Asp Ile Val Met Phe
465                 470                 475                 480
Glu Gly Ala Thr Glu Glu Lys Leu Leu Ser Arg Lys Met Met Lys
                485                 490                 495
Tyr Trp Ala Thr Phe Ala Arg Thr Gly Asn Pro Asn Gly Asn Asp Leu
            500                 505                 510
Ser Leu Trp Pro Ala Tyr Asn Leu Thr Glu Gln Tyr Leu Gln Leu Asp
        515                 520                 525
Leu Asn Met Ser Leu Gly Gln Arg Leu Lys Glu Pro Arg Val Asp Phe
    530                 535                 540
Trp Thr Ser Thr Ile Pro Leu Ile Leu Ser Ala Ser Asp Met Leu His
545                 550                 555                 560
Ser Pro Leu Ser Ser Leu Thr Phe Leu Ser Leu Leu Gln Pro Phe Phe
                565                 570                 575
Phe Phe Cys Ala Pro
            580

<210> SEQ ID NO 3
<211> LENGTH: 1746
<212> TYPE: DNA
<213> ORGANISM: Homo sapiens

<400> SEQUENCE: 3
atgccacagg gacttacttc atctgcttca caatggtgct ttttcctgat tctccagccc      60
ctgttgggac acagacagtg gggaaaaact gggccttctg ctgaagggcc acagaggaac    120
accaggctgg gatggattca gggcaagcaa gtcactgtgc tgggaagccc tgtgcctgtg    180
aacgtgttcc tcggagtccc ctttgctgct ccccgctgg gatccctgcg atttacgaac    240
ccgcagcctg catcgccctg gataacttg cgagaagcca cctcctaccc taatttgtgc    300
ctccagaact cagagtggct gctcttagat caacacatgc tcaaggtgca ttacccgaaa    360
```

```
ttcggagtgt cagaagactg cctctacctg aacatctatg cgcctgccca cgccgataca    420
ggctccaagc tccccgtctt ggtgtggttc ccaggaggtg ccttcaagac tggctcagcc    480
tccatctttg atgggtccgc cctggctgcc tatgaggacg tgctggttgt ggtcgtccag    540
taccggctag gaatatttgg tttcttcacc acatgggatc agcatgctcc ggggaactgg    600
gccttcaagg accaggtggc tgctctgtcc tgggtccaga gaacatcga gttcttcggt    660 ggggacccca gctctgtgac catctttggc gagtccgcgg gagccataag tgtttctagt    720
cttatactgt ctcccatggc caaaggctta ttccacaaag ccatcatgga gagtggggtg    780
gccatcatcc cttacctgga ggcccatgat tatgagaaga gtgaggacct gcaggtggtt    840
gcacatttct gtggtaacaa tgcgtcagac tctgaggccc tgctgaggtg cctgaggaca    900
aaaccctcca aggagctgct gaccctcagc cagaaaacaa agtctttcac tcgagtggtt    960
gatggtgctt tctttcctaa tgagcctcta gatctattgt ctcagaaagc atttaaagca   1020
attccttcca tcatcggagt caataaccac gagtgtggct cctgctgcc tatgaaggag   1080 gctcctgaga tcctcagtgg ctccaacaag tcccttgccc tccatctgat acaaaacatc   1140
ctgcacatcc cgcctcagta tttgcacctt gtggctaatg aatacttcca tgacaagcac   1200
tccctgactg aaatccgaga cagtcttctg gacttgcttg gagatgtgtt ctttgtggtc   1260
cctgcactga tcacagctcg atatcacaga gatgctggtg cacctgtcta cttctatgag   1320
tttcggcacc ggcctcagtg cttttgaagac acgaagccgg cttttgtcaa agccgaccac   1380
gctgatgaag tccgctttgt gttcggtggt gccttcctga aggggacat tgttatgttc   1440 gaaggagcca cggaggagga gaagttactg agccggaaga tgatgaaata ctgggctacc   1500
tttgctcgaa ccgggaatcc taatgggaac gacctgtctc tgtggccagc ttataatctg   1560
actgagcagt acctccagct ggacttgaac atgagcctcg acagagact caaagaaccg   1620 cgggtggatt tttggaccag caccatcccc ctgatcctgt ctgcctccga catgctccac   1680
agtcctcttt cttccttaac tttcctctct ctcctccagc cttttctttt cttttgtgct   1740
ccttga                                                              1746
```

<210> SEQ ID NO 4
<211> LENGTH: 574
<212> TYPE: PRT
<213> ORGANISM: Artificial Sequence
<220> FEATURE:
<223> OTHER INFORMATION: Consensus sequence

<400> SEQUENCE: 4

```
Gly Lys Val Arg Gly Val Asn Glu Lys Thr Asp Asn Gly Glu Gln Ser
 1               5                   10                  15

Val Tyr Ser Phe Leu Gly Ile Pro Tyr Ala Glu Pro Val Gly Asn
                20                  25                  30

Leu Arg Phe Lys Ala Pro Gln Pro Tyr Lys Glu Pro Trp Ser Asp Val
            35                  40                  45

Leu Asp Ala Thr Lys Tyr Pro Pro Ser Cys Leu Gln Asp Asp Phe
        50                  55                  60

Gly Phe Ser Leu Ser Asp Leu Lys Val Ala Leu Lys Met Leu Ser Leu
65                  70                  75                  80

Gly Trp Asn Lys Leu Val Gly Leu Lys Leu Ser Glu Asp Cys Leu Tyr
                85                  90                  95

Leu Asn Val Tyr Thr Pro Lys Asn Thr Lys Pro Asn Ser Lys Leu Pro
                100                 105                 110
```

```
Val Met Val Trp Ile His Gly Gly Phe Met Phe Gly Ser Gly His
        115                 120                 125
Ser Leu Pro Leu Ser Leu Tyr Asp Gly Glu Ser Leu Ala Arg Glu Gly
    130                 135                 140
Asn Val Ile Val Val Ser Ile Asn Tyr Arg Leu Gly Pro Leu Gly Phe
145                 150                 155                 160
Leu Ser Thr Gly Asp Asp Lys Leu Pro Gly Ser Gly Asn Tyr Gly Leu
                165                 170                 175
Leu Asp Gln Arg Leu Ala Leu Lys Trp Val Gln Asp Asn Ile Ala Ala
            180                 185                 190
Phe Gly Gly Asp Pro Asn Ser Val Thr Ile Phe Gly Glu Ser Ala Gly
        195                 200                 205
Ala Ala Ser Val Ser Leu Leu Leu Ser Asn Gly Gly Asp Asn Pro
    210                 215                 220
Pro Ser Ser Lys Gly Leu Phe His Arg Ala Ile Ser Gln Ser Gly Ser
225                 230                 235                 240
Ala Leu Ser Pro Trp Ala Ile Gln Ser Glu Ser Asn Ala Arg Gly Arg
                245                 250                 255
Ala Lys Glu Leu Ala Arg Leu Leu Gly Cys Asn Glu Thr Ser Ser Ser
            260                 265                 270
Glu Leu Leu Asp Cys Leu Arg Ser Lys Ser Ala Glu Glu Leu Leu Glu
        275                 280                 285
Ala Thr Arg Ser Phe Leu Leu Phe Glu Tyr Val Pro Phe Leu Pro Leu
    290                 295                 300
Phe Leu Ala Phe Gly Pro Val Asp Gly Asp Ala Pro Glu Ala
305                 310                 315                 320
Phe Ile Pro Glu Asp Pro Glu Glu Leu Ile Lys Glu Gly Lys Phe Ala
                325                 330                 335
Asp Val Pro Tyr Leu Ile Gly Val Thr Lys Asp Glu Gly Tyr Phe
            340                 345                 350
Ala Ala Met Leu Leu Asn Ala Ser Ser Lys Gly Glu Asp Glu Leu Lys
        355                 360                 365
Lys Glu Thr Asn Pro Asp Val Trp Leu Glu Leu Leu Lys Tyr Leu Leu
    370                 375                 380
Phe Tyr Ala Ser Glu Ala Leu Asn Ile Lys Asp Met Asp Asp Leu Ala
385                 390                 395                 400
Asp Lys Val Leu Glu Lys Tyr Pro Gly Asp Val Asp Asp Phe Ser Val
                405                 410                 415
Glu Ser Arg Lys Pro Asn Leu Gln Asp Met Leu Thr Asp Leu Leu Phe
            420                 425                 430
Lys Cys Pro Thr Arg Val Ala Ala Asp Leu His Ala Lys His Gly Gly
        435                 440                 445
Ser Pro Val Tyr Ala Tyr Val Phe Asp His Pro Ala Ser Phe Gly Ile
    450                 455                 460
Gly Gln Phe Leu Ala Lys Arg Val Asp Pro Glu Phe Gly Gly Ala Val
465                 470                 475                 480
His Gly Asp Glu Ile Phe Phe Val Phe Gly Asn Pro Leu Leu Lys Glu
                485                 490                 495
Gln Leu Tyr Lys Ala Thr Glu Glu Glu Lys Ser Ser Ser Lys Thr
            500                 505                 510
Met Met Asn Tyr Trp Ala Asn Phe Ala Lys Thr Gly Asn Pro Asn Asn
        515                 520                 525
Gly Thr Ser Asn Gly Leu Val Val Trp Pro Lys Tyr Thr Ser Glu Glu
```

-continued

```
                530             535             540
Gln Lys Tyr Ser Leu Leu Ile Leu Leu Thr Thr Ile Thr Ala Gln Lys
545                 550                 555                 560

Leu Lys Ala Arg Asp Pro Arg Lys Val Leu Cys Asn Phe Trp
                565                 570

<210> SEQ ID NO 5
<211> LENGTH: 16
<212> TYPE: PRT
<213> ORGANISM: Artificial Sequence
<220> FEATURE:
<223> OTHER INFORMATION: Exemplary motif
<221> NAME/KEY: VARIANT
<222> LOCATION: 2
<223> OTHER INFORMATION: Xaa = Gly, or Arg
<221> NAME/KEY: VARIANT
<222> LOCATION: 4-7, 9, 11, 13
<223> OTHER INFORMATION: Xaa = Any amino acid
<221> NAME/KEY: VARIANT
<222> LOCATION: 8
<223> OTHER INFORMATION: Xaa = Leu, Ile, Val, or Met
<221> NAME/KEY: VARIANT
<222> LOCATION: 10
<223> OTHER INFORMATION: Xaa = Leu, Ile, or Val
<221> NAME/KEY: VARIANT
<222> LOCATION: 15
<223> OTHER INFORMATION: Xaa = Ser, Thr, Ala, or Gly

<400> SEQUENCE: 5

Phe Xaa Gly Xaa Xaa Xaa Xaa Xaa Xaa Xaa Xaa Gly Xaa Ser Xaa Gly
1               5                   10                  15

<210> SEQ ID NO 6
<211> LENGTH: 11
<212> TYPE: PRT
<213> ORGANISM: Artificial Sequence
<220> FEATURE:
<223> OTHER INFORMATION: Exemplary motif
<221> NAME/KEY: VARIANT
<222> LOCATION: 1
<223> OTHER INFORMATION: Xaa = Glu, or Asp
<221> NAME/KEY: VARIANT
<222> LOCATION: 5
<223> OTHER INFORMATION: Xaa = Tyr, or Thr
<221> NAME/KEY: VARIANT
<222> LOCATION: 6, 8
<223> OTHER INFORMATION: Xaa = Leu, Ile, or Val
<221> NAME/KEY: VARIANT
<222> LOCATION: 7
<223> OTHER INFORMATION: Xaa = Asp, Asn, or Ser
<221> NAME/KEY: VARIANT
<222> LOCATION: 9
<223> OTHER INFORMATION: Xaa = Leu, Ile, Val, Phe, Tyr, or Trp
<221> NAME/KEY: VARIANT
<222> LOCATION: (0)...(10)
<223> OTHER INFORMATION: Xaa = Any amino acid
<221> NAME/KEY: VARIANT
<222> LOCATION: (0)...(11)
<223> OTHER INFORMATION: Xaa = Pro, Gln, or Arg

<400> SEQUENCE: 6

Xaa Asp Cys Leu Xaa Xaa Xaa Xaa Xaa Xaa Xaa
1               5                   10
```